(12) United States Patent
Huang et al.

(10) Patent No.: US 6,752,922 B2
(45) Date of Patent: Jun. 22, 2004

(54) MICROFLUIDIC CHROMATOGRAPHY

(75) Inventors: Jiang Huang, San Jose, CA (US); Hou-Pu Chou, Sunnyvale, CA (US); Marc A. Unger, South San Francisco, CA (US)

(73) Assignee: Fluidigm Corporation, South San Francisco, CA (US)

( * ) Notice: Subject to any disclaimer, the term of this patent is extended or adjusted under 35 U.S.C. 154(b) by 89 days.

(21) Appl. No.: 10/118,469

(22) Filed: Apr. 5, 2002

(65) Prior Publication Data

US 2002/0158022 A1 Oct. 31, 2002

Related U.S. Application Data

(60) Provisional application No. 60/281,937, filed on Apr. 6, 2001.

(51) Int. Cl.$^7$ ............................................. B01D 15/08
(52) U.S. Cl. ................................. 210/198.2; 210/656
(58) Field of Search ............................. 210/635, 656, 210/659, 198.2; 422/70; 436/161; 73/61.56

(56) References Cited

U.S. PATENT DOCUMENTS

| | | | | |
|---|---|---|---|---|
| 5,132,012 A | * | 7/1992 | Miura et al. ............. | 210/198.2 |
| 5,595,650 A | * | 1/1997 | Manz ....................... | 210/198.2 |
| 5,779,868 A | * | 7/1998 | Parce et al. ............... | 204/604 |
| RE36,350 E | * | 10/1999 | Swedberg et al. ......... | 210/198.2 |
| 6,408,878 B2 | * | 6/2002 | Unger et al. .............. | 137/597 |
| 6,454,924 B2 | * | 9/2002 | Jedrzejewski et al. ..... | 204/601 |
| 6,508,988 B1 | * | 1/2003 | Van Dam et al. .......... | 422/102 |
| 6,581,441 B1 | * | 6/2003 | Paul .......................... | 73/61.52 |
| 6,596,545 B1 | * | 7/2003 | Wagner et al. ............. | 436/518 |
| 6,627,076 B2 | * | 9/2003 | Griffiths ................... | 210/198.2 |
| 6,662,818 B2 | * | 12/2003 | Paul et al. .................. | 137/14 |
| 6,664,104 B2 | * | 12/2003 | Pourahmadi et al. ..... | 435/288.6 |

FOREIGN PATENT DOCUMENTS

WO    WO01/01025    * 1/2001    .............. 210/198.2

OTHER PUBLICATIONS

Quake, Science vol.290 Nov. 2000, pp. 1536–1540.*
Van De Pol, Sensors and Actuators, 17 (1989), pp. 139–143.*
Unger, Science vol. 288 Apr. 2000, pp. 113–116.*
Remco Swart et al., *Trends in Anal. Chem.*, 1997, 16, 332–342.
Xindu Geng et al., *J. of Chromatography*, 1984, 296, 15–30.
Stephen C. Jacobson et al., *Anal. Chem.*, 1994, 66, 2369–2373.
Paul G. Vahey et al., *Talanta*, 2000, 51, 1205–1212.

* cited by examiner

*Primary Examiner*—Ernest G. Therkorn
(74) *Attorney, Agent, or Firm*—Townsend and Townsend and Crew LLP

(57) ABSTRACT

The present invention is directed to a microfluidic chromatography apparatus comprising a microfabricated fluid delivery system and a chromatography column which is in fluid communication with the fluid delivery system, and a method for producing and using the same. Preferably, the chromatography column comprises an OTLC, PCLC, or combinations thereof.

14 Claims, 15 Drawing Sheets

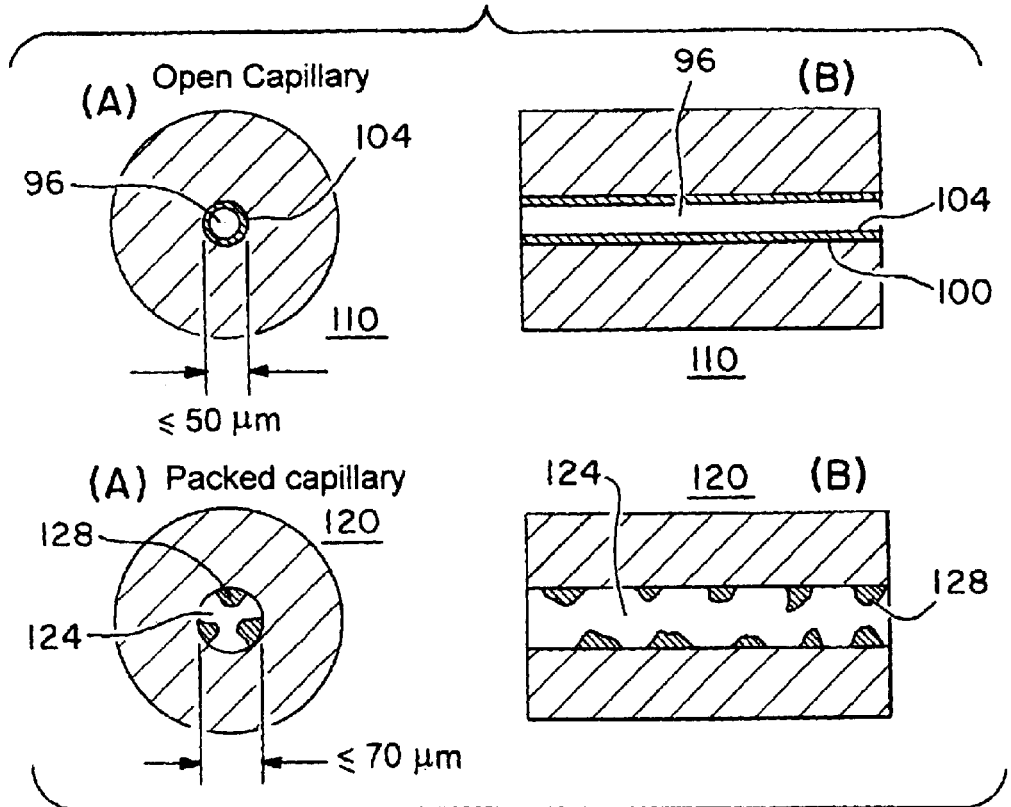
Fig. 1
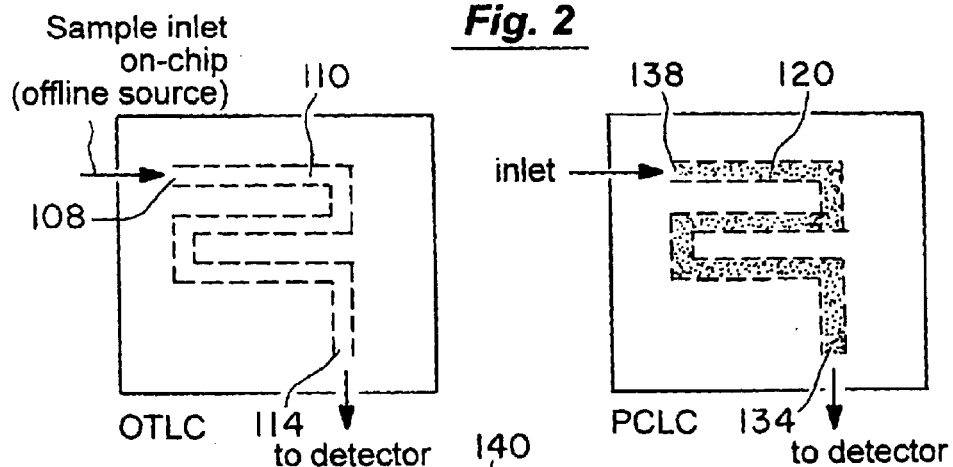
Fig. 2
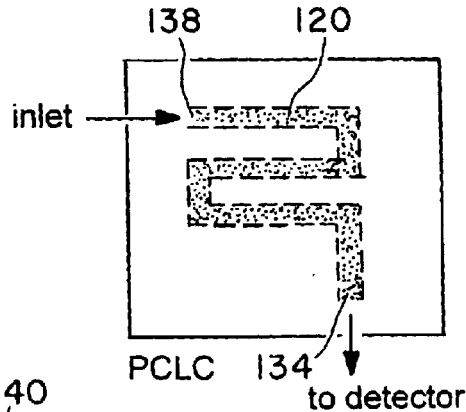
Fig. 3
Fig. 4
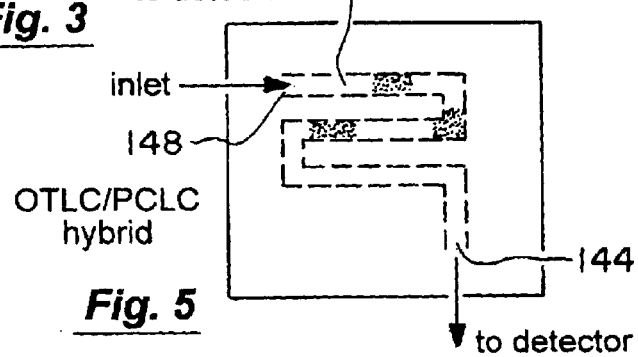
Fig. 5

(a)

(b)

MICROFLUIDIC CHROMATOGRAPHY

CROSS-REFERENCES TO RELATED APPLICATIONS

This application claims the benefit of U.S. Provisional Patent Application Ser. No. 60/281,937, filed Apr. 6, 2001.

FIELD OF THE INVENTION

The present invention relates to a microfluidic device comprising a microfabricated fluid delivery system and a chromatography column. In particular, the present invention relates to a microfluidic device comprising an OTLC column, PCLC column, or combinations thereof, which is operatively interconnected to a microfabricated fluid delivery system.

BACKGROUND OF THE INVENTION

Microfluidic devices allow manipulation of extremely small volumes of liquids, and therefore are particularly useful in small scale sample preparations, chemical synthesis, sample assay, sample screening, and other applications where a micro-scale amount of samples are involved. For many applications, the chemical make up of the resulting material (i.e., sample) needs to be analyzed. Such analysis typically requires at least some degree of sample purification and/or separation. However, due to the small sample size (e.g., nanoliter to microliter) used by these microfluidic devices, conventional separation techniques are not applicable.

Use of packed capillary and open tubular liquid chromatography (PCLC and OTLC, respectively) separation techniques have become increasingly popular due to the demonstrated means of achieving high chromatography efficiency with low operation pressures. Conventional high performance liquid chromatography (i.e., HPLC) typically requires >2000 psi pressure. In contrast, pressure of as low as 5 psi can be used for OTLC and PCLC. Some of the advantages of the OTLC and PCLC techniques include, but are not limited to: (1) an increased efficiency, (2) a lower sample dilution requirement, thereby increasing the sample detection sensitivity, e.g., using a mass spectrometer, (3) a smaller amount of eluent requirement, and (4) the small sample amount requirement. The latter advantage is of particularly importance in a variety of fields, such as proteomics, genomics, forensics, and other areas where a minute quantity of sample is to be separated or purified. Unfortunately, in order to achieve the desired sensitivity and efficiency in OTLC and PCLC, the inner diameter of OTLC and PCLC columns need to be small, generally in the order of 50 $\mu$m or less, and preferably about 10 $\mu$m or less. The small column diameter size in OTLC and PCLC techniques requires an equally precise sample injection and pumping system. To be effective, OTLC and PCLC techniques require a sample flow rate of 0.01 $\mu$L/min or less. Conventional sample pumping system can not adequately meet this stringent requirement. In addition, difficulties with large interconnection dead volume and detection volume between the OTLC or PCLC column and the fluid delivery (i.e., pumping) system have greatly limited the application of OTLC and PCLC techniques.

Therefore, there is a need for OTLC and PCLC devices which comprise a sample injection and fluid pumping system that can achieve a sample flow rate of 0.01 $\mu$L/min or less. There is also a need for OTLC and PCLC devices which have small or no dead volume between the OTLC or PCLC column and the fluid delivery system.

SUMMARY OF THE INVENTION

One aspect of the present invention provides a microfluidic chromatography apparatus for separating an analyte in a sample fluid. The microfluidic chromatography apparatus of the present invention comprises a microfabricated fluid delivery system and a chromatography column. The microfabricated fluid delivery system of the present invention is capable of pumping a minute amount of fluid through the chromatography column. Preferably, the microfabricated fluid delivery system is capable of pumping (i.e., delivering or transporting) a fluid through the chromatography column at a flow rate of 0.01 $\mu$L/min or less. Thus, microfluidic chromatography apparatuses of the present invention are particularly useful in separating analyte(s) from a minute quantity of sample fluid.

Preferably, the fluid delivery system of the present invention is produced from a material comprising an elastomeric polymer. In one particular embodiment, the elastomeric polymer is selected from the group consisting of poly(carborane-siloxanes), poly(bis(fluoroalkoxy)phosphazene), poly(acrylonitrile-butadiene), poly(1-butene), poly(chlorotrifluoroethylene-vinylidene fluoride) copolymers, poly(ethyl vinyl ether), poly(vinylidene fluoride), poly(vinylidene fluoride-hexafluoropropylene) copolymer, elastomeric polyvinylchloride, polysulfone, polycarbonate, polymethylmethacrylate, polytertrafluoroethylene, polydimethylsiloxane, polydimethylsiloxane copolymer, and aliphatic urethane diacrylate.

The fluid deliver system of the present invention comprises:

(i) a microfluidic flow channel comprising a flow channel inlet for introducing the fluid into said flow channel and a flow channel outlet, (ii) a flow control channel, (iii) a flow control valve comprised of a flow control elastomeric segment that is disposed in between said flow channel and said flow control channel to regulate fluid flow through said flow channel, wherein said flow control valve is deflectable into or retractable from said flow channel upon which said flow control valve operates in response to an actuation force applied to said flow control channel, said flow control elastomeric segment when positioned in said flow channel restricting fluid flow therethrough, and (iv) a flow control channel actuation system operatively interconnected to said flow control channel for applying an actuation force to said flow control channel.

The fluid delivery system of the present invention can further comprise other component(s) depending on a particular need. For example, in one particular embodiment, the fluid delivery system further comprises a peristaltic pump which is comprised of one or more of the flow control valves.

The fluid delivery system can also comprise an eluent inlet which is in fluid communication with the flow channel inlet for introducing an eluent to said flow channel. In one specific embodiment, the eluent inlet further comprises:

an eluent reservoir comprising an eluent reservoir inlet channel;

an eluent reservoir inlet control channel;

an eluent reservoir inlet control valve for opening and closing fluid communication between said eluent reservoir and said flow channel, wherein said eluent reservoir inlet control valve comprises an elastomeric segment of said eluent reservoir inlet control channel that is disposed in between said eluent reservoir inlet control channel and said eluent reservoir inlet channel to regulate fluid flow through said eluent reservoir inlet channel, wherein said eluent reservoir inlet control valve is deflectable into or retractable from said eluent reservoir inlet channel upon which said eluent reservoir inlet control valve operates in response to an actuation force applied to said eluent reservoir inlet control channel, said elastomeric segment of said eluent reservoir inlet control valve when positioned in said eluent reservoir inlet channel restricting fluid flow therethrough;

an eluent reservoir inlet control channel actuation system operatively interconnected to said eluent reservoir inlet control channel for applying an actuation force to said eluent reservoir inlet control channel.

The flow channel inlet of the fluid delivery system can also comprise:

a sample reservoir comprising a sample reservoir inlet channel which is in fluid communication with said flow channel;

a sample reservoir inlet control channel;

a sample reservoir inlet control valve for opening and closing fluid communication between said sample reservoir and said flow channel, wherein said sample reservoir inlet control valve comprises an elastomeric segment of said sample reservoir inlet control channel that is disposed in between said sample reservoir control channel and said sample reservoir inlet channel to regulate fluid flow through said sample reservoir inlet channel, wherein said sample reservoir inlet control valve is deflectable into or retractable from said sample reservoir inlet channel upon which said sample reservoir inlet control valve operates in response to an actuation force applied to said sample reservoir inlet control channel, said elastomeric segment of said sample reservoir inlet control channel when positioned in said sample reservoir inlet channel restricting fluid flow therethrough; and an sample reservoir inlet control channel actuation system operatively interconnected to said sample reservoir inlet control channel for applying an actuation force to said sample reservoir inlet control channel.

The chromatography column of the present invention comprises:

(i) a stationary phase which is capable of separating at least a portion of the analyte from the sample fluid, (ii) a column inlet which is in fluid communication with said flow channel outlet, and (iii) a column outlet through which a separated fluid exits the chromatography column.

Preferably, the chromatography column is a separately fabricated component which is then integrated with the microfabricated fluid delivery system. Advantages of this embodiment include the capability of using the microfabricated fluid delivery system with a variety of different chromatography columns and interchangeability of chromatography columns depending on the need. Thus, in one particular embodiment, the chromatography column is a microfluidic chromatography device comprising a chromatography channel having an inner surface. Preferably, the stationary phase is covalently bonded to the inner surface of the chromatography channel. The stationary phase can be bonded to the chromatography column by a variety of means conventionally known to one skilled in the art. Such methods include activating or depositing ions on the inner surface of the column. Preferably, the stationary phase is bonded to the inner surface of the column without the need for any surface activation process. In this manner, an integrated microfluidic chromatography system can be fabricated.

In one embodiment, the chromatography column comprises a microfabricated rotary channel comprising:

a rotary channel inlet;

a rotary channel outlet;

a rotary control channel;

a rotary inlet control valve comprised of an elastomeric segment of said rotary inlet control channel that is disposed in between said rotary channel inlet and said rotary control channel to regulate fluid flow into said rotary channel, wherein said rotary inlet control valve is deflectable into or retractable from said rotary channel inlet upon which said rotary inlet control valve operates in response to an actuation force applied to said rotary control channel, said elastomeric segment of said rotary inlet control channel when positioned in said rotary channel inlet restricting fluid flow therethrough;

a rotary outlet control valve comprised of an elastomeric segment of said rotary outlet control channel that is disposed in between said rotary channel outlet and said rotary control channel to regulate fluid flow out of said rotary channel, wherein said rotary outlet control valve is deflectable into or retractable from said rotary channel outlet upon which said rotary outlet control valve operates in response to an actuation force applied to said rotary control channel, said elastomeric segment of said rotary control channel outlet when positioned in said rotary channel outlet restricting fluid flow therethrough;

a rotary pump valve comprised of an elastomeric segment of said rotary pump that is disposed in between said rotary channel and said rotary pump control channel to regulate fluid flow through said rotary channel, wherein said rotary pump valve is deflectable into or retractable from said rotary channel upon which said rotary pump valve operates in response to an actuation force applied to said rotary pump control channel, said elastomeric segment of said rotary pump when positioned in said rotary channel restricting fluid flow therethrough; and a rotary control channel actuation system operatively interconnected to said rotary control channel for applying an actuation force to said rotary control channel.

In one particular embodiment, the chromatography column is an open tubular liquid chromatography column or a packed capillary liquid column or a combination of these two columns.

The column outlet can also be in fluid communication with a sample detection system inlet. In this manner, the fluid exiting the chromatography column can be analyzed directly with a detection apparatus.

Furthermore, other components, such as sample preparation and detection components, can be fabricated or incorporated within the microfluidic chromatography apparatus of the present invention to provide parallel-processing systems.

In one embodiment of the present invention, the flow channel is located on an interface between a solid substrate and the elastomeric polymer such that an inner surface of the flow channel comprises an elastomeric polymer portion and a solid substrate portion. In one particular embodiment, the stationary phase is attached to the solid substrate portion of the flow channel inner surface. In one specific embodiment, the elastomeric polymer portion of the flow channel inner surface comprises a surface coating that reduces a non-specific binding of the analyte.

Another aspect of the present invention provides a method for producing the microfluidic chromatography apparatus. In one particular embodiment, such a method comprises:

(a) producing a microfabricated fluid delivery system from a material comprising an elastomeric polymer, wherein the fluid deliver system comprises:
   (i) a microfluidic flow channel comprising a flow channel inlet for introducing the fluid into said flow channel and a flow channel outlet,
   (ii) a flow control channel,
   (iii) a flow control valve comprised of a flow control elastomeric segment that is disposed in between said flow channel and said flow control channel to regulate fluid flow through said flow channel, wherein said flow control valve is deflectable into or retractable from said flow channel upon which said flow control valve operates in response to an actuation force applied to said flow control channel, said flow control elastomeric segment when positioned in said flow channel restricting fluid flow therethrough, and
   (iv) a flow control channel actuation system operatively interconnected to said flow control channel for applying an actuation force to said flow control channel; and
(b) connecting the fluid delivery system to a chromatography column having a column inlet and a column outlet such that the column inlet is in fluid communication with the flow channel outlet, wherein the chromatography column comprises a stationary phase which is capable of separating at least a portion of the analyte in the fluid.

In addition, methods for producing the microfluidic chromatography apparatus can further include (a) microfabricating the chromatography column which comprises a chromatography channel having an inner surface which comprises a functional group; and
(b) attaching a stationary phase compound to at least a portion of the inner surface by reacting the stationary phase compound with the functional group under conditions sufficient to form a covalent bond between the functional group and the stationary phase compound.

In one particular embodiment, the functional group is silane.

In another embodiment, the stationary phase compound is 1-octadecene.

The method can also include microfabricating a rotary channel described above.

Yet another aspect of the present invention provides a method for separating an analyte from a sample fluid comprising:

(a) introducing the sample fluid into a microfluidic chromatography a apparatus described above, and
(b) eluting the sample fluid through the chromatography column with an eluent to separate at least a portion of the analyte.

In one particular embodiment, fluid flow through the chromatography column is achieved by a peristaltic pump action created by actuating one or more of the flow control valves.

When the chromatography column comprises a microfabricated rotary channel, the method can further include:
introducing at least a portion of the sample fluid into the rotary channel;

closing the rotary inlet and the rotary outlet control valves by actuating the rotary inlet and the rotary outlet control valves;

transporting the sample fluid through the rotary channel by actuating one or more of the rotary pump valves until at least a portion of the analyte is adsorbed onto the stationary phase;

opening the rotary inlet and rotary outlet control channels;

introducing a first eluent through the rotary inlet channel and removing the resulting mixture through the rotary outlet channel, whereby substantially all of the sample fluid is removed from the rotary channel and at least about 95% of the adsorbed analyte remains adsorbed onto the stationary phase; and introducing a second eluent, which is capable of removing the analyte from the stationary phase, through the rotary inlet channel and removing the resulting mixture through the rotary outlet channel, whereby substantially all of the adsorbed analyte is removed from the rotary channel.

Such rotary channel chromatography column is particularly useful in separating a large molecules such as proteins and oligonucleotides. In one particular embodiment, the analyte is a protein having a molecular weight of at least about 1000 g/mol. Suitable stationary phases for proteins and oligonucleotides are well known to one skilled in the art. For example, proteins in aqueous solution can be separated using C-18 alkyl as the stationary phase. In this manner, the first eluent is selected from the group consisting of water and an aqueous buffer solution, which removes the sample fluid but substantially leaves the adsorbed proteins bound to the solid phase. By using a second eluent which comprises an organic solvent selected from the group consisting of an alcohol, acetonitrile, dimethylformamide, and mixtures thereof, one can then remove the protein from the stationary phase. The second eluent can also be a mixture of the organic solvent and water or an aqueous buffer solution.

BRIEF DESCRIPTION OF THE DRAWINGS

FIG. 1A is a front view illustration of an open capillary comprising a covalently bound surface modifying compound as a stationary phase.

FIG. 1B is a side cross-sectional view illustration of an open capillary comprising a covalently bound surface modifying compound as a stationary phase.

FIG. 2A is a front view illustration of a packed capillary comprising a covalently bound surface modifying compound as a stationary phase.

FIG. 2B is a side cross-sectional view illustration of a packed capillary comprising a covalently bound surface modifying compound as a stationary phase.

FIG. 3 is an illustration of a microfluidic chromatography apparatus comprising an open capillary.

FIG. 4 is an illustration of a microfluidic chromatography apparatus comprising an a packed capillary.

FIG. 5 is an illustration of a microfluidic chromatography apparatus comprising both open capillary and packed capillary portions.

DEFINITION

Figure 6:
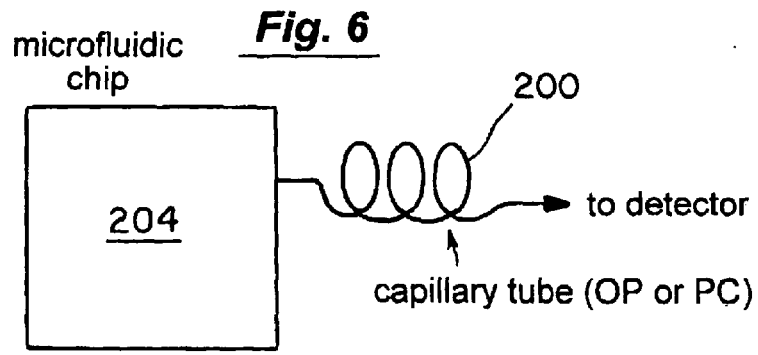
FIG. 6 is an illustration of a microfluidic device operatively interconnected to a capillary tube.

The terms "reactive polymerizable functional group", "polymerizable functional group", and "functional group" are used interchangeably herein and refer to a functional group present in the monomeric or prepolymer or pre-crosslinked polymer unit(s) of the polymer which react to form a polymer. It should be appreciated that the reactive functional group refers to a functional group that is inherently present in the polymer without any additional treatment, e.g., activation, of the polymer. Exemplary reactive functional groups include, but are not limited to, silane, alkene, isocyanate, epoxide, hydroxyl, and the like.

"Complimentary reactive polymerizable functional group" refers to a functional group present in each polymer component, i.e., monomer or prepolymer or pre-crosslinked polymer, that react with each other to form a polymer.

"Active functional group" of a stationary phase compound refers to a functional group present in the stationary phase compound which reacts with the functional group of the polymer to form a covalent bond. Exemplary active functional groups include, but are not limited to, hydroxy, alkene, silane, epoxide, isocyanate, and the like.

"Off ratio polymer" refers to a polymer which is produced from a combination of two or more monomeric or prepolymer or pre-crosslinked polymer units in which at least one monomeric component is present in excess of the other component(s).

"Biocompatible polymer" refers to a polymer which when exposed to a cell does not significantly change the cell morphology, cell and protein activity, and other cellular functions.

"Distribution equilibrium" refers to the ratio of the amount of a substrate bound, i.e., adhered, to the stationary phase of the column or the fluid flow channel and the amount of the substrate dissolved in the solution.

"Rotary" refers to a configuration of a channel which allows circulation of a fluid within a confined region or section of the channel. Such configuration can be a polygon, such as rectangle, hexagon, octagon, and the like; or, preferably, an ellipse or a circle.

The terms "microfabricated flow channel," "flow channel," "fluid channel," and "fluid flow channel" are used interchangeably herein and refer to a channel in a microfluidic device in which a fluid, such as gas or, preferably, liquid, can flow through.

The terms "chromatography column" and "column" are used interchangeably herein and refers to a device or an apparatus which comprises a stationary phase that is capable of separating at least a portion of an analyte in a fluid.

The term "valve" unless otherwise indicted refers to a configuration in which two channels are separated by an elastomeric segment that can be deflected into or retracted from one of the channels in response to an actuation force applied to the other channel.

DETAILED DESCRIPTION OF THE INVENTION

One aspect of the present invention provides a microfluidic chromatography apparatus, a method for producing the same, and a method for using the same. Preferably, the microfluidic chromatography apparatus of the present invention comprises a microfabricated fluid delivery system and a chromatography column, preferably an OTLC column, PCLC column, or combinations thereof. The chromatography column can be an integral part of the microfabricated fluid delivery system and as such it can be microfabricated within the microfabricated fluid delivery system. Preferably, the chromatography column can be fabricated separately and integrated into the microfabricated fluid delivery system. The microfabricated fluid delivery system of the present invention is capable of delivering the fluid at a flow rate of 100 $\mu$L/min or less, preferably 10 $\mu$L/min or less, and more preferably 1 $\mu$L/min or less.

The microfabricated fluid delivery system of the present invention is produced from a polymer, preferably an elastomeric polymer. In one particular embodiment of the present invention, the microfabricated fluid delivery system is typically constructed at least in part from elastomeric materials and constructed by single and multilayer soft lithography (MLSL) techniques and/or sacrificial-layer encapsulation methods. See, for example, Unger et al. (2000) Science 288:113–116, U.S. patent application Ser. No. 09/605,520, filed Jun. 27, 2000, and PCT Publication No. WO 01/01025, all of which are incorporated by reference herein in their entirety. Thus, the microfluidic devices of the present invention comprise a microfabricated fluid flow channel (i.e., flow channel or fluid flow channel).

In one aspect, the chromatography column itself is also produced from a microfluidic device by modifying the inner surface of the chromatography channel. In one embodiment, the chromatography column comprises a stationary phase which is covalently attached to the inner surfacace of the chromatography channel. Preferably, the stationary phase is covalently bonded to the inner surface. The stationary phase modifies the inner surface characteristics of the chromatography channel such that it is capable of separating an analyte from a sample fluid. Depending on the particular stationary phase (i.e., surface modifying compound) used, the chromatography column can be used in reverse phase, normal phase, hydrophobic interaction, affinity, etc., chromatography. Thus, a variety of chromatography columns can be fabricated by selecting an appropriate stationary phase compound. Typically, the stationary phase is selected based on a particular analyte to be separated from the sample fluid.

Conventional surface coated polymers require activating the polymer surface before forming a bond with a surface modifying compound (e.g., stationary phase compound). In contrast, microfluidic chromatography column devices of the present invention are preferably made from polymers such that the resulting chromatography column devices comprise a functional group within the inner surface of the chromatography channel. Thus, in one embodiment, microfluidic chromatography column devices of the present invention do not require a separate inner surface activation step for covalent bonding the stationary phase compound. The stationary phase is covalently bonded to the chromatography channel by forming a covalent bond between an active functional group of the stationary phase compound and the functional group of the polymer. As stated above, the functional group is inherently present on the polymer surface prior to contacting it with a stationary phase compound, and therefore a separate activation step is not required. The amount of functional group on the inner surface of the chromatography channel should be sufficient enough such that a useful chromatography column is formed by reacting with a stationary phase compound. Typically on the average, polymers that are used to produce microfluidic chromatography column devices of the present invention comprise at least one functional group per 10,000 monomeric units on the inner surface of the chromatography channel. Preferably, polymers of the present invention comprise at least one functional group per 1,000 monomeric units on the inner surface. And more preferably, polymers of the present invention comprise at least one functional group per 100 monomeric units on the inner surface.

In one aspect of the present invention, the microfluidic devices (e.g., fluid delivery devices and/or chromatography column devices) are produced from polymers by combining two or more different polymer components (e.g., monomers) in which each polymer component includes a complimentary reactive functional group. The ratio of each component is selected such that there is an excess of at least one component to provide unreacted function group within the polymer surface, including any inner surface. Preferably, polymers of the present invention comprise at least one polymerizable functional group per 10,000 monomeric units within the polymer bulk matrix. More preferably, polymers of the present invention comprise at least one polymerizable functional group per 1,000 monomeric units within the polymer bulk matrix. And most preferably, polymers of the present invention comprise at least one polymerizable functional group per 100 monomeric units within the polymer bulk matrix.

Stationary Phase Compound

It has been found by the present inventors that by using "off ratio polymers" with the quantity of unreacted functional group described above, a stationary phase compound with an appropriate activate function group can be covalently attached to the polymer surface without the need for a polymer surface activation step. Such off ratio polymers are disclosed in the commonly assigned co-pending U.S. Provisional Patent Application Ser. No. 60/281,929, entitled "Polymer Surface Modification," filed on Apr. 6, 2001 which is incorporated herein by reference in its entirety. However, it should be appreciated that depending on the particular polymer used, the process for producing microfluidic devices of the present invention can also include activating the polymer surface for covalent linkage with a stationary phase compound. For example, such a surface activation is particularly desirable where the column is fabricated from a different material than the fluid delivery system.

Stationary phase compounds are selected such that the resulting column is capable of separating at least a portion of the desired analyte from the sample fluid. Suitable stationary phase compounds for a particular analyte are well known to one skilled in the art. For example, useful stationary phase compounds include, but are not limited to, 1-octadecanol, 1-octadecene, octadecylsilane, octadecyltrichlorosilane, octadecyl isocyanate, trioctedecylsilane, etc. for $C_{18}$ grafting (e.g., stationary phase for $C_{18}$ reverse phase LC), and corresponding compounds for $C_8$, $C_4$ or $C_2$ stationary phase.

The stationary phase compounds can be attached to the inner surface of the column by contacting the stationary phase compound to the inner surface under conditions sufficient to produce a covalent bond. For example, attachment of 1-octadecene to a polymer comprising a silane functional group (e.g., Si—H) can be achieved by contacting, e.g, immersing, spraying, or coating, the polymer with 1-octadecene which have a terminal olefin group. The silane group reacts with the olefin group to form an alkyl-silane bond to produce a C-18 stationary phase column. In one particular embodiment of the present invention, the stationary phase compound is useful in forming an OTLC column, PCLC column, or mixtures thereof.

Typically, at least about 1 equiv. of the stationary phase compound is used, preferably at least about 10 equiv., and more preferably at least about 100 equiv. As used herein, the equiv. of the stationary phase compound refers to the equiv. amount of the functional group of the stationary phase compound relative to the theoretical amount of the functional group present on the polymer surface to be treated. Use of an excess amount of the stationary phase compound ensures a substantially complete and a relatively fast surface coating. Any excess stationary phase compound that is not covalently attached to the inner surface is then removed from the column.

When forming a covalent bond with the functional group of the polymer, the stationary phase compound can be in the form of a solution in an inert solvent. Or if the stationary phase compound is a liquid or a gas, it can be used directed without any solvent. When the stationary phase compound is in a solution, the solvent used is, preferably, inert to the reaction conditions. Suitable inert solvents for a particular reactive functional group are well known to one of ordinary skill in the art. For example, suitable inert solvents for a silane reactive functional group include hydrocarbons, ethyl ether, tetrahydrofuran, dimethoxyethane (DME), dimethyl formaldehyde, chloroform, dichloromethane, toluene, xylene, and the like.

The reaction temperature between the intrinsic functional group of the polymer and the stationary phase compound depends on a variety of factors including, the stability of the polymer at a particular temperature, concentration and reactivity of the function groups, the stability of the covalent bond that is formed, etc. For example, in reacting 1-octadecene to a polymer comprising a silane group, the reaction temperature is typically from about 20° C. to about 200° C., preferably from about 50° C. to about 150° C., and more preferably from about 70° C. to about 90° C.

The reaction time also depends on a variety of factors such as concentration of the functional group and the stationary phase compound, reaction temperature, reactivity of the functional group and the stationary phase compound, etc. For reacting 1-octadecene to a polymer comprising a silane group, the reaction time is typically from about 2 h to about 60 h, preferably from about 8 h to about 48 h, and more preferably from about 12 h to about 24 h.

Basic Features of the Microfluidic Fluid Delivery System

In one particular aspect of the present invention, microfluidic devices are constructed at least in part from elastomeric materials. Typically, the microfluidic devices are constructed by single and multilayer soft lithography (MLSL) techniques and/or sacrificial-layer encapsulation methods as disclosed in the above incorporated U.S. patent application Ser. No. 09/605,520, filed Jun. 27, 2000, PCT Publication No. WO 01/01025, and Unger et al. (2000) Science 288:113–116.

Microfluidic devices of the present invention comprise a microfabricated flow channel. In addition, microfluidic devices of the present invention can optionally further comprise a variety of plumbing components (e.g., pumps, valves, and connecting channels) for flowing fluids such as reagents, solvents, and samples. The microfluidic devices can also comprise an array of reservoirs for storing reaction reagents (e.g., solvents, samples, eluents, and other reagents can each be stored in a different reservoir).

The microfluidic devices of the present invention have a basic "flow channel" structure. The term "flow channel", "fluid channel", or "microfabricated flow channel" refers to a channel in which a fluid, such as gas or, preferably, liquid, can flow through. The flow channels can also be actuated to function as the plumbing components (e.g., micro-pumps, micro-valves, or connecting channels) of the microfluidic devices.

In some applications, microfabricated flow channels are cast on a chip (e.g., a elastomeric chip). Fluid channels are formed by bonding the chip to a flat substrate (e.g., a glass cover slip or another polymer) which seals the channel. Thus, one side of the synthesis channel is provided by the flat substrate. Typically, the stationary phase compound is attached to the inner surface of the polymer within the chromatography channel. However, when the flow channel is formed by attaching the polymer to a solid substrate, such as glass, the inner surface of the flow channel comprises a polymer portion and a solid substrate portion. In essence, the flow channel is formed on an interface between the polymer and the solid substrate. In one embodiment, the solid stationary phase is covalently bonded to the solid substrate. The surface of the solid substrate (i.e., inner surface of the solid substrate portion of the flow channel) can be etched or modified to include arrays of pillars, columns, pyramides, etc. to increase the surface area of the chromatography column. Such surface modifications of a solid substrate can be readily achieved using standard wafer/glass process steps. In another embodiment, the polymer portion of the flow channel inner wall is coated with a surface modifying compound to reduce non-specific bonding (NBS) of the analyte, i.e., passivated. Alternatively, the solid substrate portion can be passivated and the polymer portion can be covalently bonded to the stationary phase compound.

The plumbing components can be microfabricated as described in the above incorporated references. For example, the microfluidic devices can contain an integrated flow cell (i.e., reservoir) in which a plurality of fluid channels are present, and fluidic components (such as micropumps, micro-valves, and connecting channels) for controlling the flow of the reagents into and out of the flow cell. Alternatively, the microfluidic devices of the present invention can utilize other plumbing devices. See for example, Zdeblick et al., A Microminiature Electric-to-Fluidic Valve, Proceedings of the 4th International Conference on Solid State Transducers and Actuators, 1987; Shoji et al., Smallest Dead Volume Microvalves for Integrated Chemical Analyzing Systems, Proceedings of Transducers '91, San Francisco, 1991; and Vieider et al., A Pneumatically Actuated Micro Valve with a Silicon Rubber Membrane for Integration with Fluid Handling Systems, Proceedings of Transducers '95, Stockholm, 1995, all of which are incorporated herein by reference in their entirety.

At least some of the components of the microfluidic devices are microfabricated. Employment of microfabricated fluid channels and/or microfabricated plumbing components significantly reduce the dead volume and decrease the amount of time needed to exchange reagents, which in turn increase the throughput. Microfabrication refers to feature dimensions on the micron level, with at least one dimension of the microfabricated structure being less than 1000 $\mu$m. In some microfluidic devices, only the fluid channels are microfabricated. In some microfluidic devices, in addition to the fluid channels, the valves, pumps, and connecting channels are also microfabricated. Unless otherwise specified, the discussion below of microfabrication is applicable to production of all microfabricated components of the microfluidic devices (e.g., the fluid channels, valves, pumps, and connecting channels).

As discussed in detail below, various materials can be used to produce the microfluidic devices. Preferably, elastomeric materials are used. Thus, in some microfluidic devices, the integrated (i.e., monolithic) microstructures are made out of various layers of elastomer bonded together. By bonding these various elastomeric layers together, the recesses extending along the various elastomeric layers form fluid channels through the resulting monolithic, integral elastomeric structure.

In general, the microfabricated structures (e.g., fluid channels, pumps, valves, and connecting channels) have widths of about 0.01 to 1000 microns, and a width-to-depth ratios of between 0.1:1 to 100:1. Preferably, the width is in the range of 10 to 200 microns, a width-to-depth ratio of 3:1 to 15:1.

Microfluidic Chromatography

Carrying out chemical or biochemical analyses, syntheses or preparations, even at the simplest levels, requires one to perform a large number of separate manipulations on the material components of that analysis, synthesis or preparation, including measuring, aliquoting, transferring, diluting, concentrating, separating, detecting, etc. In this respect, microfluidic devices of the present invention are particularly useful in performing these manipulations, particularly in separation of the analyte, in a microscale level.

In order to manipulate reagents (e.g., samples, eluents, etc.) within the microfabricate devices described herein, the overall microfabricate devices of the present invention typically include a pumps, valves, various channels, and/or chambers. Pumps and valves generally are designed to controls the movement and direction of fluids within the flow channel. Generally, pump and valve systems employ pressure or other known actuation systems to affect fluid movement and fluid flow direction. Preferably, the microfluidic devices of the present invention comprise the pump and valve systems, which are described in detail below. Other fluid movement and direction controls for microfluidic devices are known in the art, including mechanical pumps and valves and electroosmotic fluid direction systems. Such fluid movement and direction controls are contemplated to be within the scope of the present invention. Electroosmotic fluid direction systems and controllers are well known and described in detail, for example, in U.S. Pat. No. 5,779,868, which is incorporated herein by reference in its entirety.

The present invention will be described with regard to the accompanying drawings which assist in illustrating various features of the invention. In this regard, the present invention generally relates to microfluidic chromatography apparatuses. In one aspect of the present invention, microfluidic devices of the present invention comprise an OTLC column, PCLC column, or combinations thereof. It should be appreciated that the drawings are provided for the purpose of illustrating the practice of the present invention and do not constitute limitations on the scope thereof.

Referring to FIGS. 1A and 1B, OTLC column 110 comprises a flow channel 96 having an inner surface 100 and a stationary phase 104 which comprises a stationary phase compound covalently bonded to the inner surface 100. The stationary phase 104 is capable of separating an analyte in a solution, and as such the selection of a particular stationary phase compound depends on the particular analyte to be separated.

FIGS. 2A and 2B illustrate PCLC 120 which comprises a chromatography channel 124 packed with a solid adsorbent 128. The solid adsorbent 128 can comprise a solid polymer, e.g., plastic, glass, and other polymers, which is coated or, preferably, covalently bonded to a stationary phase compound. Alternatively, the solid adsorbent 128 can be a conventional chromatography adsorbent such as paper, cellulose, starch, sugars, magnesium silicate, calcium sulfate, silicic acid, silica gel, florisil, magnesium oxide, aluminum oxide (alumina), activated charcoal, and the like. It should be appreciated these conventional chromatography adsorbents are not coated or covalently bonded to a separate stationary phase compound. In these adsorbents, their surface contains moieties, e.g., functional group such as hydroxy groups, that effect separation of the analyte. In conventional PCLC columns, the solid adsorbent 128 is typically not bound to the inner surface of the chromatography channel 124, which can result in the solid adsorbent 128 leaking out of the chromatography channel 124 during its operation. Leakage of the solid adsorbent 128 from the chromatography channel 124 can be prevented by tapering the outlet portion of the chromatography channel 124.

Preferably, the solid adsorbent 128 in PCLC 120 is an integral part of the microfluidic chromatography channel and is covalently bonded to a stationary phase compound, i.e., the solid adsorbent 128 comprises a plurality of protuberances that are present on the inner surface of the chromatography channel. Thus, the solid adsorbent 128 comprises a same polymeric material as the microfluidic chromatography column itself which is covalently bonded to a stationary phase compound. Such a chromatography channel can be readily fabricated by using a mold having a non-smooth surface, e.g., mold having protuberances or depressions, or other suitable polymer fabrication techniques known to one skilled in the art. Thus, in this embodiment, the chromatography channel 124 is technically not "packed" but is comprised of a plurality of inner surface protuberances within the inner surface of the chromatography channel 124. One of the advantages for having a plurality of protuberances within the inner surface is an increase in the total surface area of the inner surface of the chromatography channel 124, which results in a longer net effective column length and a higher net effective column plate number.

It should be appreciated that the microfluidic devices of the present invention can comprise a plurality of OTLC columns, PCLC columns, or combinations thereof. Such plurality of columns can be arranged in series, see FIG. 5, to provide separation of a number of analytes within a single sample fluid. They can also be arranged in parallel (not shown) to provide separation of a number of solutions in a single microfluidic device. Or the columns can be arranged in both series and parallel manner (not shown) to allow separation of a number of analytes from a number of sample fluids on a singe microfluidic device.

FIGS. 3, 4 and 5 correspond to microfluidic devices comprising an OTLC column, PCLC column and a combination of OTLC and PCLC columns, respectively. A sample (neat or in a solution) is introduced through the inlets 108, 138 and 148 of FIGS. 3, 4 and 5, respectively. A pump and valve system (not shown) moves the sample through the columns 110, 120 and 140 (shown in phantom). An eluent can be introduced through the same inlet 108, 138 and 148 or the microfluidic devices can further comprise an eluent inlet and an eluent reservoir (not shown) that is interconnected to the columns 110, 120, and 140 near the inlets 108, 138 and 148, respectively. A pump and valve system (not shown) can be used to control the flow of eluent through the columns 110, 120 and 140. As the solutes (i.e., analyte) passes down the columns 110, 120 and 140 a kind of distribution equilibrium is established between the stationary phase (i.e., adsorbent material or surface modifying compound) and the solvent. The distribution equilibrium refers to the equilibrium established between the solute being adsorbed onto the stationary phase and the amount of solute dissolved in the solvent. Such distribution equilibrium depends on the strength of interaction between the solute and the stationary phase, and the solubility of the solute in a given solvent. Useful solvents for a particular stationary phase and analyte are well known to one skilled in the art or can be readily determined without undue experimentation. Typically, different solutes have different distribution equilibrium. Therefore, different solutes will move down the columns 110, 120 and 140 at differing rates depending on their relative affinity for the adsorbent (i.e., stationary phase) on one hand and for the solvent on the other. As the components of the mixture (i.e., analytes) are separated, they begin to form moving bands or zones. Preferably, the length of columns 110, 120 and 140 are chosen such that the bands are separated from one another, leaving gaps of pure solvent in between. The outlets 114, 134 and 144 can be interconnected to a detector, such as gas chromatography, IR, UV/VIS, or Mass Spectrometer, for analyzing the separated solute. Alternatively, the outlets 114, 134 and 144 can be interconnected to another microfluid device which can further manipulate the separated sample, e.g., PCR amplification of nucleotides.

In one aspect, the microfluidic chromatography column device and the microfabricated fluid delivery system are fabricated separately and integrated with each other such that one microfluidic device serves as a fluid delivery or injection system and the other is used as chromatography column. Advantages of this aspect of the invention include the capability of using the microfabricated fluid delivery systems with a variety of different chromatography columns and interchangeability of chromatography columns depending on the need. One such embodiment is illustrated in FIG. 6, where a chromatography column 200 is operatively interconnected to a microfluidic device 204. This allows use of the microfluidic device 204 with a various chromatography columns and applications. The microfluidic devices 204 can comprise a variety of components, such as a component for sample concentration, sample dilution, sample preparation components, etc.

In one aspect of the present invention, commercially available chromatography columns can be purchased and used in conjunction with the microfluidic device 204. Such OTLC and PCLC columns can be readily produced without difficulties. Referring again to FIG. 6, the chromatography column 200 can be interconnected to the microfluidic device 204 simply by inserting the column 200 in to the flow channel (not shown) of the microfluidic device 200. In this manner, the column 200 sits within the flow channel (not shown) and extends beyond the edge of the microfluidic device 204. The length of the column 200 depends on a variety of factors including, but not limited to, the amount of column length required to separate the analyte from the sample.

Figure 7A:
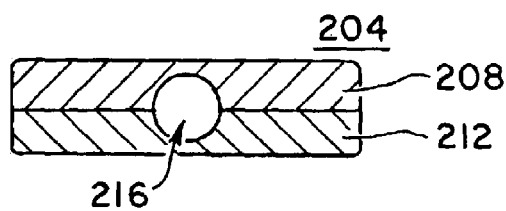
FIG. 7A is a front view of the first elastic layer integrated with a chromatography column.
Figure 7B:
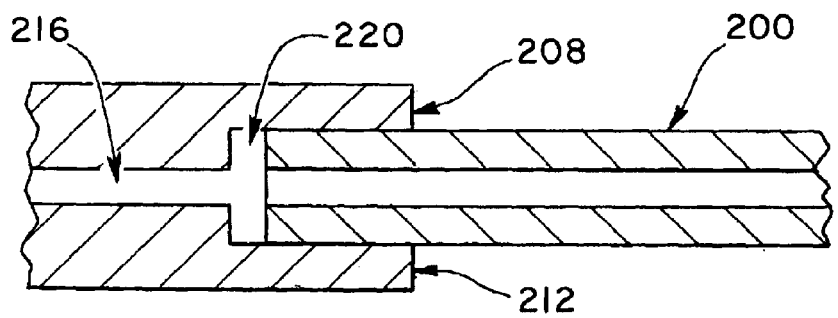
FIG. 7B is a side cross-sectional view showing the first elastic layer fitted with a chromatography column with dead volume in between the fluid channel and the chromatography column.
Figure 7C:
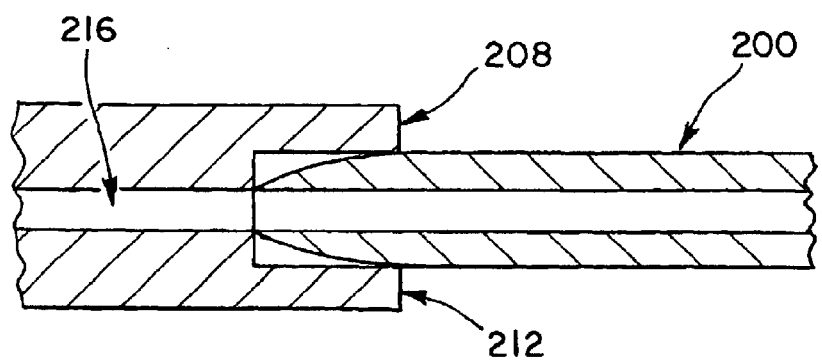
FIG. 7C is a side cross-sectional view showing the first elastic layer fitted with a chromatography column having a tapered fitting end which reduces the amount of dead volume.

As shown in FIGS. 7A–7C, the column 200 can be sealed within two portions (i.e., layers 208 and 212) of the microfluidic device 204. It can be sealed either directly by baking together the two portions of partially cured elastomers or by incorporation of uncured elastomer (e.g., RTV, discussed in detail below) during the final bake (i.e., curing) stage. In this arrangement, fluids are designed to flow in the middle of the two portions (i.e., top portion 208 and bottom portion 212) of the microfluidic device 204. The alignment of the column 200 between the two portions and its juxtaposition with the fluid channel 216 can create a partial occlusion of the capillary when the column 200 is centered between the layers. Better alignments can be achieved by creating an offset in the depths (i.e., height) of two portions of the channels between which the capillary is fitted. For example, if the depth of the lower portion is 5 microns less than the upper portion of the polymer, a column with a ten-micron internal diameter can be accommodated without a significant offset.

The portion of flow channel 216 that becomes integrated with the column 200 is configured such that the fluid sample flows directly from the microfluidic device 204 to the column 200. And the column 200 can be further interconnected to a sample analytical device, a collection device, or another microfluidic device(s) for further manipulation of the separated analyte (not shown). Additional features patterned in polymer may be necessary to reduce potential dead volume 220 at the junction between the column 200 and the flow channel 216. Alternatively, the amount of dead volume can be reduced by using a tapered column 200 as shown in FIG. 7C. Typical, dimensions of the OTLC or PCLC columns that can be accommodated in microfluidic devices of the present invention include, but are not limited to, columns with internal diameters of from about 500 $\mu$m to about 2 $\mu$m and outer diameters of from about 1000 $\mu$m to about 10 $\mu$m.

Figure 8A:
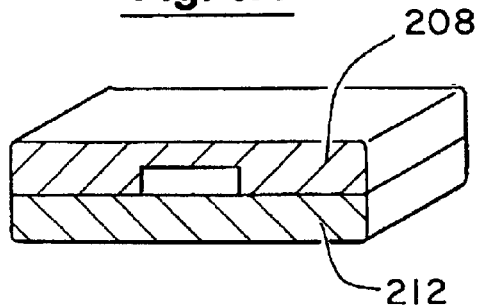
FIG. 8A is a perspective view of the first elastic layer having a rectangular cross-section fluid flow channel.
Figure 8B:
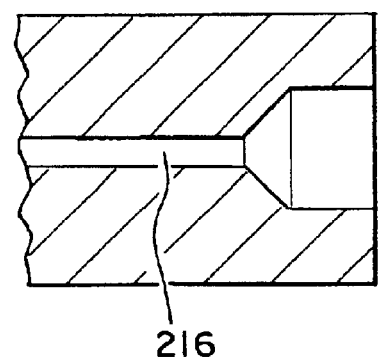
FIG. 8B is a cut-away view along 1–1' of FIG. 41A showing a tapered portion of fluid flow channel which is designed to reduce the amount of dead volume between the chromatography column and the fluid flow channel.
Figure 8C:
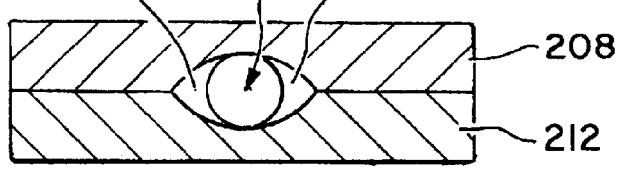
FIG. 8C is a front view of the first elastic layer fitted with a chromatography column illustrating a possible gap formation between the chromatography column and the fluid flow channel.
Figure 9:
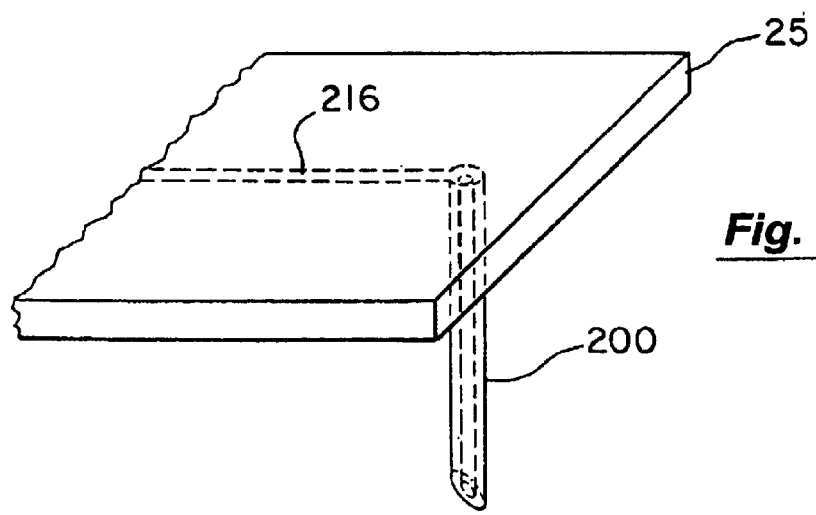
FIG. 9 is another embodiment of attaching a chromatography column to a microfluidic device of the present invention through the Z-axis.

The column 200 can be sealed within the microfluidic device 204, by a variety of processes. For example, the column 200 can be sealed during baking together of the two portions of the elastic layers. Alternatively, as shown in FIGS. 8A–8C, the column 200 is 'push-fit' into the microfluidic device 204 having a slightly smaller flow channel diameter than the outer diameter of the column 200, thereby creating an instant seal. The dimensions of the push-fit envelope are chosen to accommodate the diameter of the column 200. For example, an envelope of about 200 μm width and about 15 μm in height has a perimeter of 430 microns. A column 200 with 100 μm outer diameter has a circumference of 314 μm. The seal can be further secured by incorporation of uncured elastomer (e.g., RTV) in the envelope between the two portions (e.g., areas 224A and 224B in FIG. 8C). As shown in FIG. 9, push fitting can also be used to incorporate a column 200 that fits into the device in the 'Z' plane. One major advantage of push fitting is that column 200 can be easily interchanged if clogging occurs.

Chromatography separation results depend on many factors including, but not limited to, the adsorbent (i.e., stationary phase compound) chosen, polarity of the solvent, size of the column (both length and diameter) relative to the amount of material to be chromatographed, and the rate of elution. Columns shown in FIGS. 3, 4 and 5 are single pass columns, i.e., samples and solutions travel through the column only once during operation. Thus, in some cases a long column or multiple columns arranged in series may be required to separate the sample effectively. This is particularly true when the sample has a relatively low distribution equilibrium between the stationary phase and the solvent. In other cases, the sample can bind tightly to the adsorbent material and may require a different solvent to elute the sample from the adsorbent. For example, proteins/peptides with molecular weight of greater than 1000 in aqueous medium bind tightly to C-18 alkyl stationary phase. This bonding is so strong that it is difficult to effectively remove the protein from the stationary phase using water. Typically an organic eluent, such as acetonitrile, alchohol (e.g., methanol, ethanol, or isopropanol), other relatively polar organic solvents (e.g., DMF), or mixtures thereof, is used as an eluent to remove the protein from the stationary phase.

Figure 10:
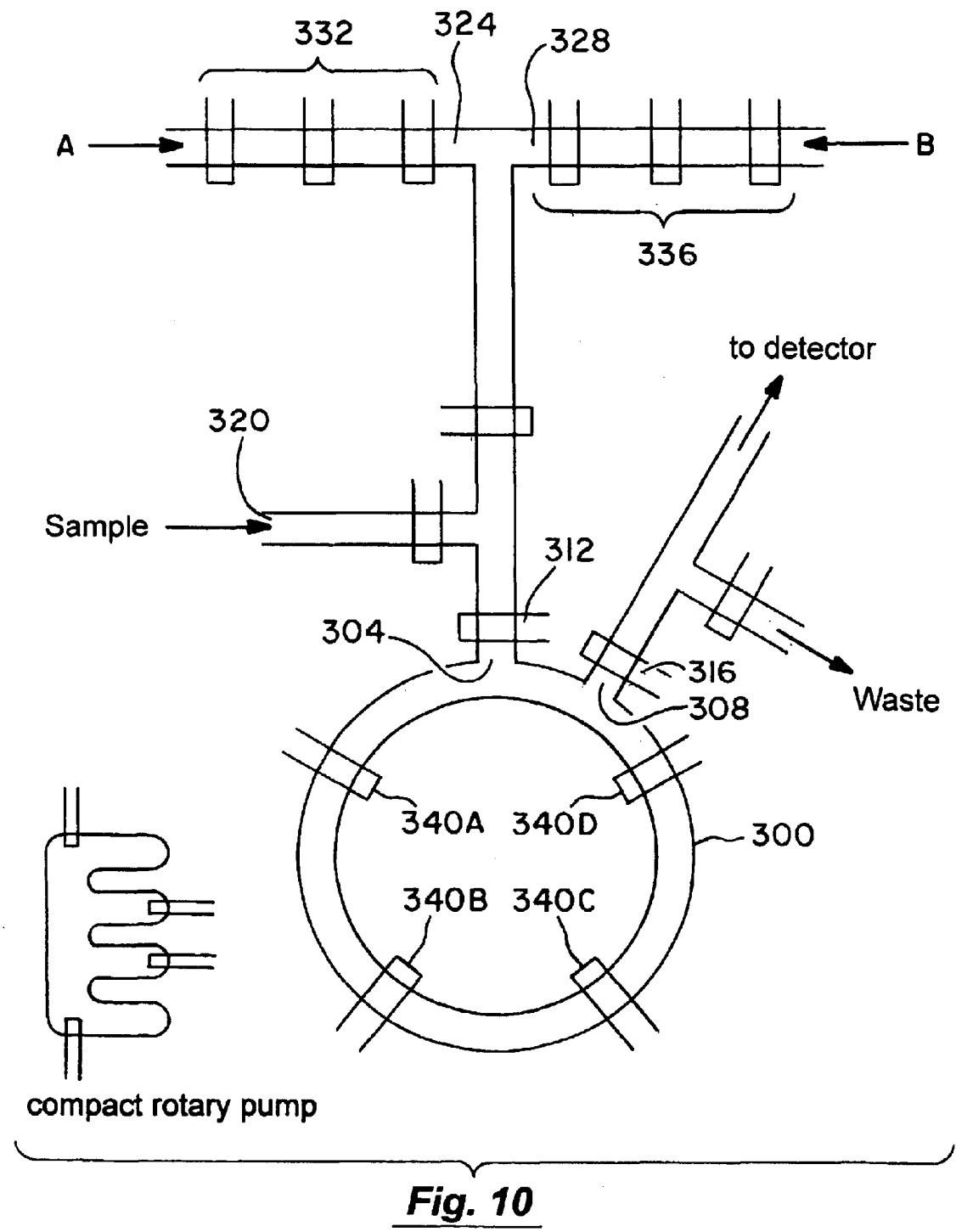
FIG. 10 is an illustration of a rotary pump chromatography column of a microfluidic device of the present invention.

Present inventors have found that this difference in the distribution equilibrium of samples, e.g., proteins, in different solvents can be used advantageously with microfluidic devices of the present invention in some sample separations. One such configuration is illustrated in FIG. 10 which will be described in reference to separating proteins. However, it should be appreciated that other compounds having a similar distribution equilibrium difference in different solvents can be separated using the principle disclosed herein.

The microfluidic device of FIG. 10 comprises a rotary flow channel 300 which has an inlet 304 and an outlet 308. The flow channel 300 is covalently bonded to a stationary phase compound, such as C-18 alkyl, that binds strongly to proteins in aqueous solution. An aqueous protein solution is introduced into the rotary flow channel 300 by opening the control valves 312 and 316. If the volume of the sample is insufficient to completely fill the rotary flow channel 300, additional water can be added through the inlet 304. Water can be introduced through the same sample port 320 or, as shown in FIG. 10, a separate solvent port 324 can be present in the microfluidic devices. Optionally, the microfluidic devices can further comprise an additional solvent port 328 for introducing a second solvent which can be mixed with the first solvent that is introduced through the solvent port 324. Preferably, each solvent port has its own pump and control valve systems 332 and 336.

After the rotary flow channel 300 is filled with the aqueous protein solution, control valves 312 and 316 are actuated to maintain a closed system. The aqueous protein solution is then circulated through the rotary flow channel using a pump comprised of control valves 340A–340D until substantially all the high molecular proteins are bound to the inner surface of the flow channel 300. The rotary flow channel 300 can be flushed with water by opening the control valves 312 and 316 and introducing additional water through the inlet 304 and removing the solution through the outlet 308. The exiting solution can he connected to other rotary flow channel(s) (not shown) to further separate other compounds that may be present, discarded, collected, or sent to a detector system to identify the contents of the exiting solution. At this stage, high molecular proteins are bound to the inner surface of the rotary flow channel 300 and low molecular proteins and other polar compounds have been removed from the rotary flow channel 300. To recover the bound protein, acetonitrile, methanol, ethanol or mixtures thereof, or an aqueous mixture of such solvent is introduced to the rotary flow channel 300 through the inlet 312. Presence of organic solvent lowers the distribution equilibrium between the stationary phase and the solvent, i.e., the amount of protein in the solution is increased. The organic solution containing dissolved proteins can be collected, analyzed, or further manipulated as needed. Alternatively, after introducing the organic solvent, control valves 312 and 316 can be closed and the solvent circulated through the rotary fluid channel 300 prior to removing the solution from the rotary fluid channel 300. This allows dissolution of proteins in a small volume of the organic solvent.

Basic Methods of Microfabrication

Figures 11, 12:
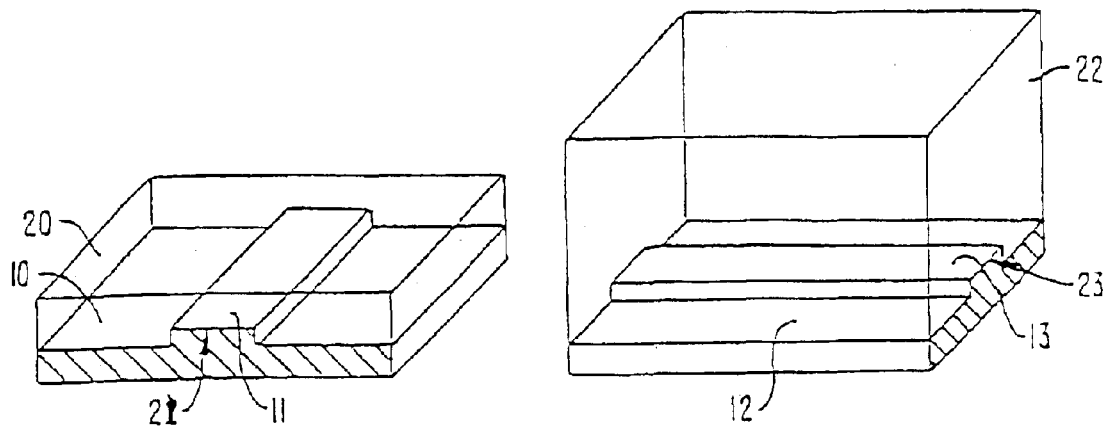
FIG. 11 is an illustration of a first elastomeric layer formed on top of a micromachined mold.
FIG. 12 is an illustration of a second elastomeric layer formed on top of a micromachined mold.

Various methods can be used to produce the microfabricated components of the microfluidic devices of the present invention. Fabrication of the microchannels, such as flow channels, valves, and pumps, can be performed as described in the above incorporated references. In some methods, e.g., FIGS. 11 to 17B, pre-cured elastomer layers are assembled and bonded to produce a flow channel. As illustrated in FIG. 11, a first micro-machined mold 10 is provided. Micro-machined mold 10 can be fabricated by a number of conventional silicon processing methods including, but not limited to, photolithography, ion-milling, and electron beam lithography. The micro-machined mold 10 has a raised line or protrusion 11 extending therealong. A first elastomeric layer 20 is cast on top of mold 10 such that a first recess 21 can be formed in the bottom surface of elastomeric layer 20, (recess 21 corresponding in dimension to protrusion 11), as shown.

As can be seen in FIG. 12, a second micro-machined mold 12 having a raised protrusion 13 extending therealong is also provided. A second elastomeric layer 22 is cast on top of mold 12, as shown, such that a recess 23 can be formed in its bottom surface corresponding to the dimensions of protrusion 13.

Figure 13:
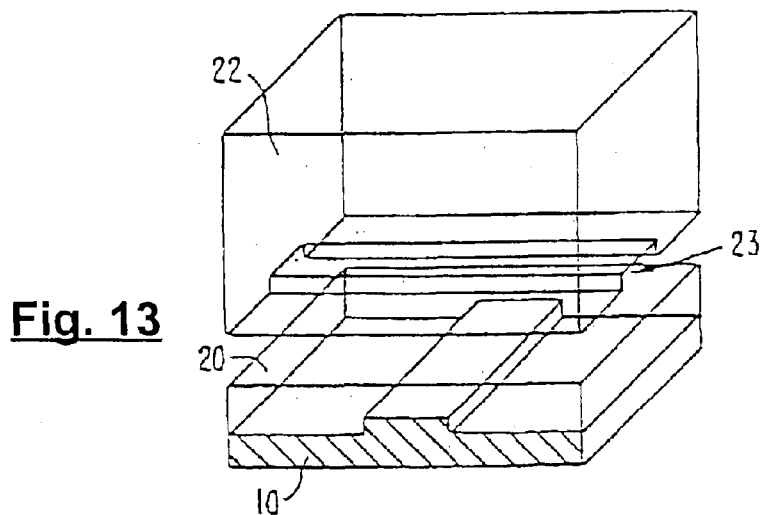
FIG. 13 is an illustration of the elastomeric layer of FIG. 12 removed from the micromachined mold and positioned over the top of the elastomeric layer of FIG. 1
Figure 14:
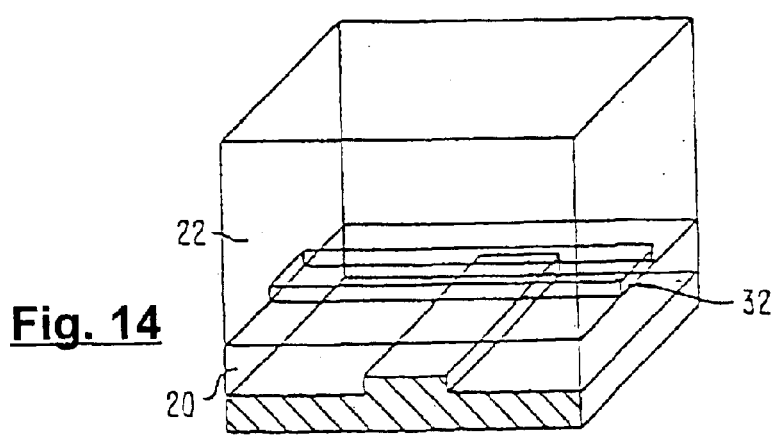
FIG. 14 is an illustration corresponding to FIG. 13, but showing the second elastomeric layer positioned on top of the first elastomeric layer.

As can be seen in the sequential steps illustrated in FIGS. 13 and 14, second elastomeric layer 22 is then removed from mold 12 and placed on top of first elastomeric layer 20. As can be seen, recess 23 extending along the bottom surface of second elastomeric layer 22 forms a control channel 32.

Figure 15:
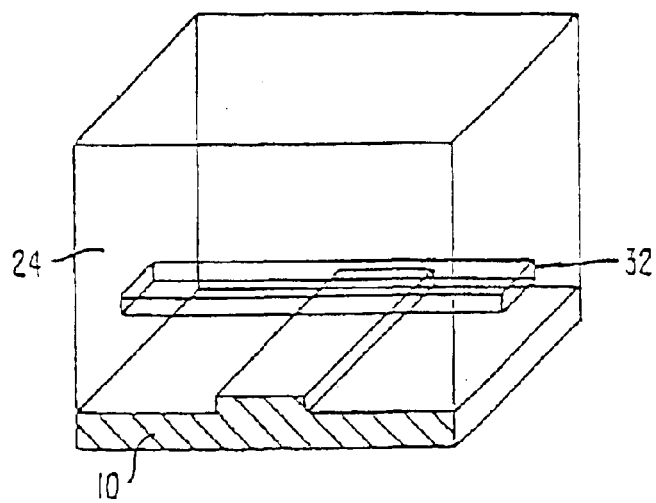
FIG. 15 is an illustration corresponding to FIG. 14, but showing the first and second elastomeric layers bonded together.

Referring to FIG. 15, the separate first and second elastomeric layers 20 and 22 (FIG. 14) are then bonded together to form an integrated (i.e., monolithic) elastomeric structure 24.

Figure 16:
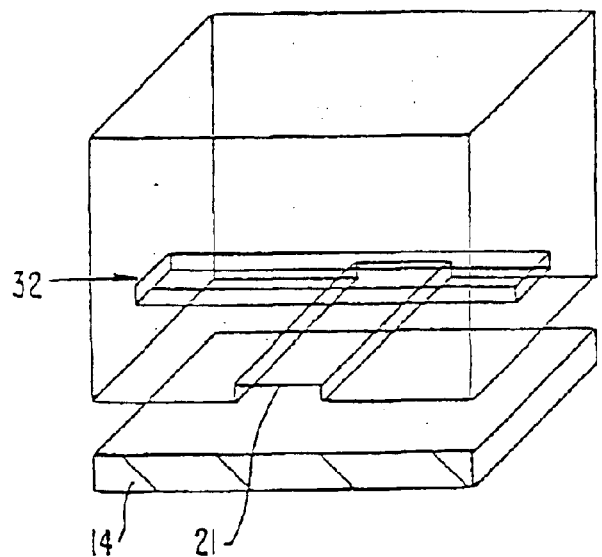
FIG. 16 is an illustration corresponding to FIG. 15, but showing the first micromachined mold removed and a planar substrate positioned in its place.
Figure 17A:
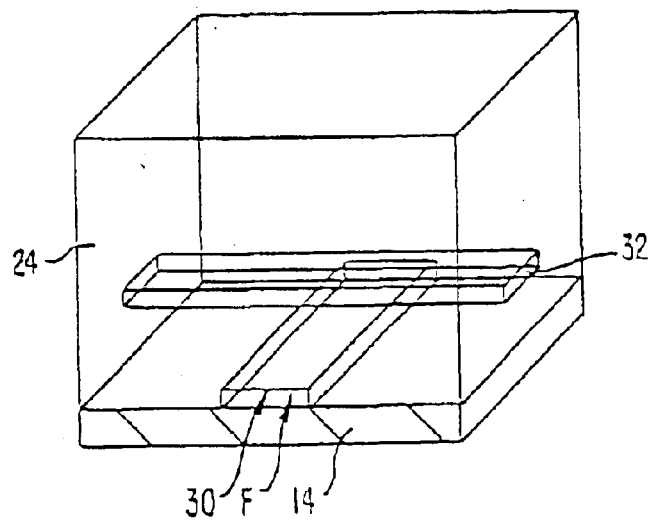
FIG. 17A is an illustration corresponding to FIG. 16, but showing the elastomeric structure sealed onto the planar substrate.
Figure 17B:
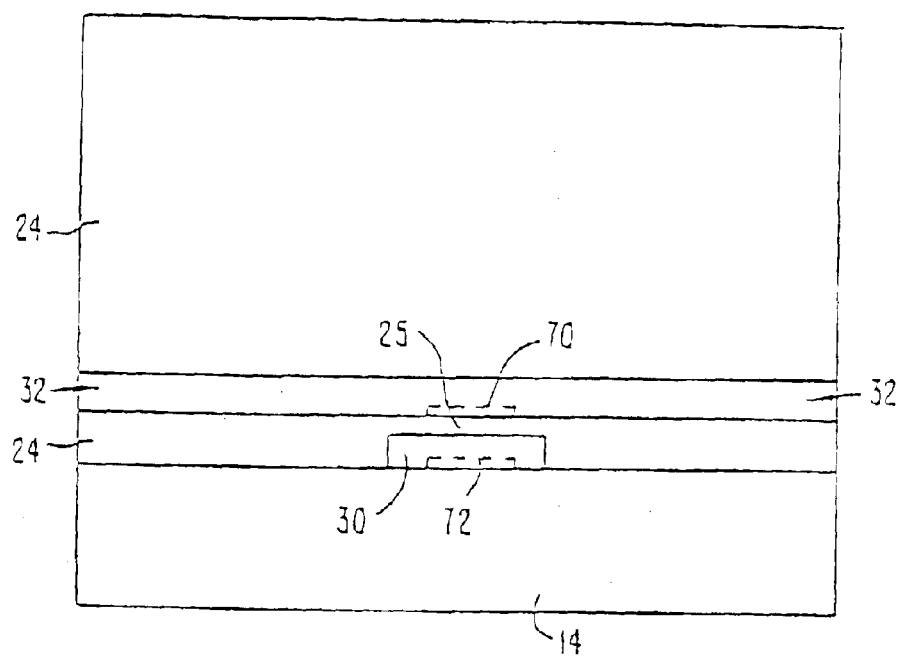
FIG. 17B is a front sectional view corresponding to FIG. 17A, showing an open flow channel.
Figure 17C:
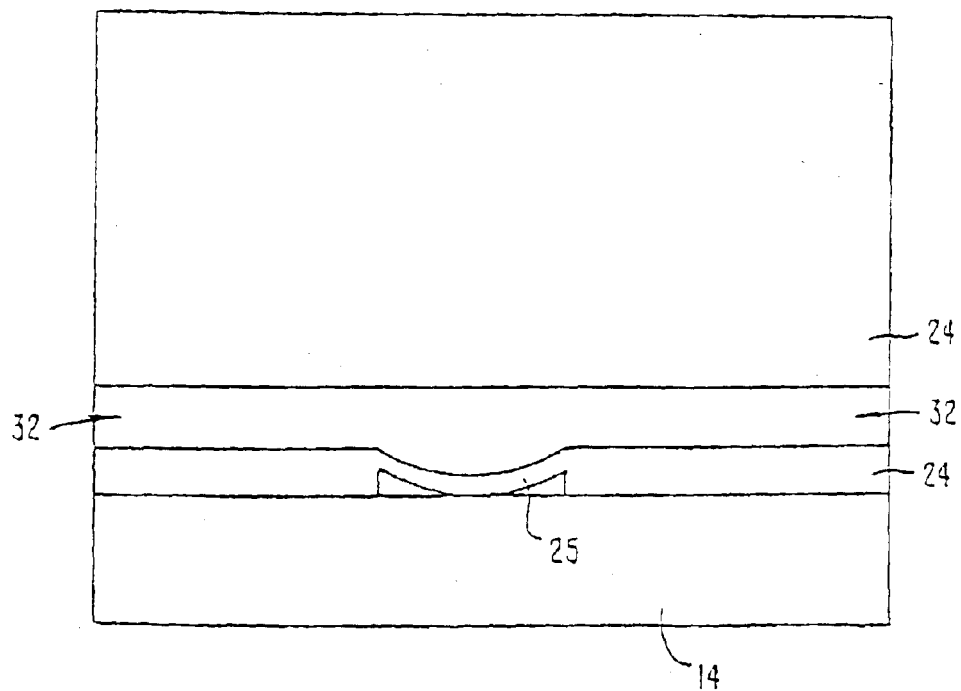
FIG. 17C corresponds to FIG. 17A, but shows a first flow channel closed by pressurization in second flow channel.

As can been seen in the sequential step of FIGS. 16 and 17A, elastomeric structure 24 is then removed from mold 10 and positioned on top of a planar substrate 14. As can be seen in FIGS. 17A and 17B, when elastomeric structure 24 has been sealed at its bottom surface to planar substrate 14, recess 21 forms a flow channel 30.

The present elastomeric structures can form a reversible hermetic seat with nearly any smooth planar substrate. An advantage to forming a seal this way is that the elastomeric structures can be peeled up, washed, and re-used. In some microfluidic devices, planar substrate 14 is glass. A further advantage of using glass is that glass is transparent, allowing optical interrogation of elastomer channels and reservoirs. Alternatively, the elastomeric structure can be bonded onto a flat elastomer layer by the same method as described above, forming a permanent and high-strength bond. This can prove advantageous when higher back pressures are used.

In some methods, microfabrication involves curing each layer of elastomer "in place" (FIGS. 18 to 28). In these methods, fluid flow and control channels are defined by first patterning sacrificial layer on the surface of an elastomeric layer (or other substrate, which can include glass) leaving a raised line of sacrificial layer where a channel is desired. Next, a second layer of elastomer is added thereover and a second sacrificial layer is patterned on the second layer of elastomer leaving a raised line of sacrificial layer where a channel is desired. A third layer of elastomer is deposited thereover. Finally, the sacrificial layer is removed by dissolving it out of the elastomer with an appropriate solvent, with the voids formed by removal of the sacrificial layer becoming the flow channels passing through the substrate, i.e., microfluidic device.

Figure 18:
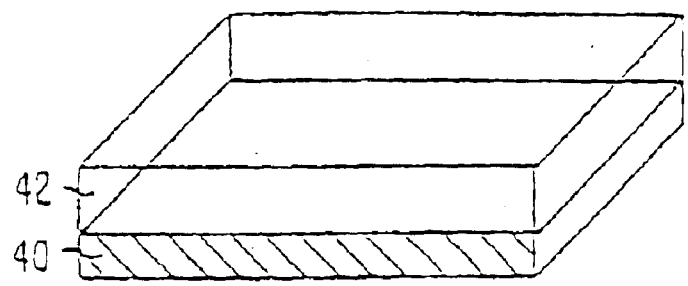
FIG. 18 is an illustration of a first elastomeric layer deposited on a planar substrate.
Figure 19:
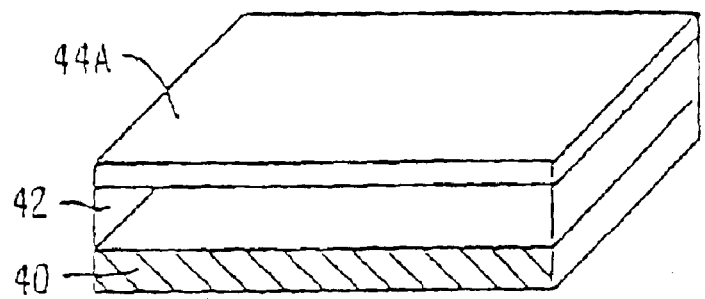
FIG. 19 is an illustration showing a first sacrificial layer deposited on top of the first elastomeric layer of FIG. 18.
Figure 20:
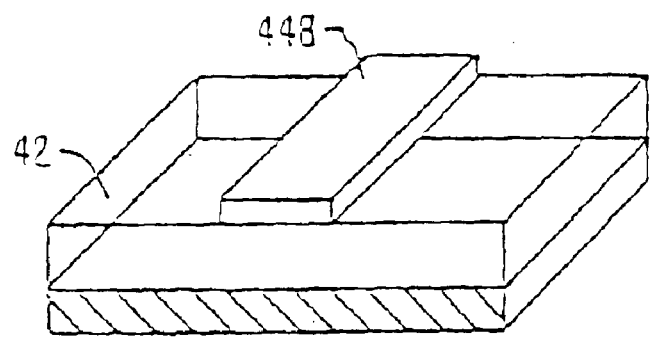
FIG. 20 is an illustration showing the system of FIG. 19, but with a portion of the first sacrificial layer removed, leaving only a first line of sacrificial layer.
Figure 21:
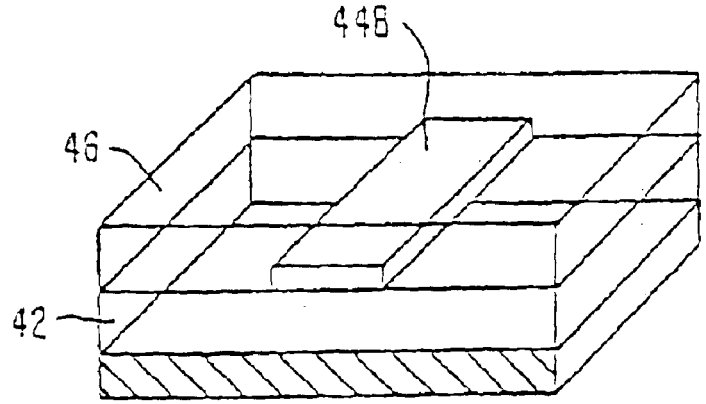
FIG. 21 is an illustration showing a second elastomeric layer applied on top of the first elastomeric layer over the first line of sacrificial layer of FIG. 20, thereby encasing the sacrificial layer between the first and second elastomeric layers.
Figure 22:
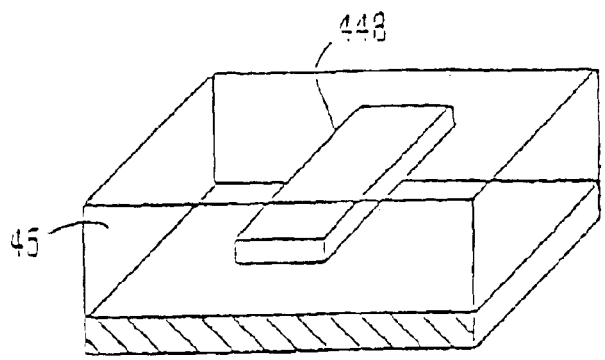
FIG. 22 corresponds to FIG. 21, but shows the integrated monolithic structure produced after the first and second elastomer layers have been bonded together.

Referring first to FIG. 18, a planar substrate 40 is provided. A first elastomeric layer 42 is then deposited and cured on top of planar substrate 40. Referring to FIG. 19, a first sacrificial layer 44A is then deposited over the top of elastomeric layer 42. Referring to FIG. 20, a portion of sacrificial layer 44A is removed such that only a first line of sacrificial layer 44B remains as shown. Referring to FIG. 21, a second elastomeric layer 46 is then deposited over the top of first elastomeric layer 42 and over the first line of sacrificial layer 44B as shown, thereby encasing first line of sacrificial layer 44B between first elastomeric layer 42 and second elastomeric layer 46. Referring to FIG. 22, elastomeric layers 46 is then cured on layer 42 to bond the layers together to form a monolithic elastomeric substrate 45.

Figure 23:
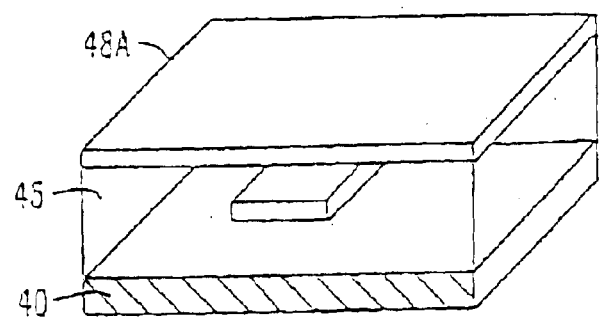
FIG. 23 is an illustration showing a second sacrificial layer deposited on top of the integral elastomeric structure of FIG. 22.
Figure 24:
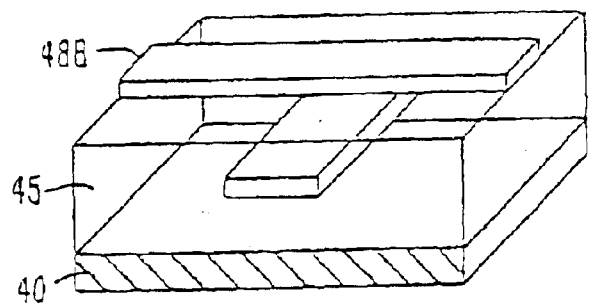
FIG. 24 is an illustration showing the system of FIG. 23, but with a portion of the second sacrificial layer removed, leaving only a second line of sacrificial layer.
Figure 25:
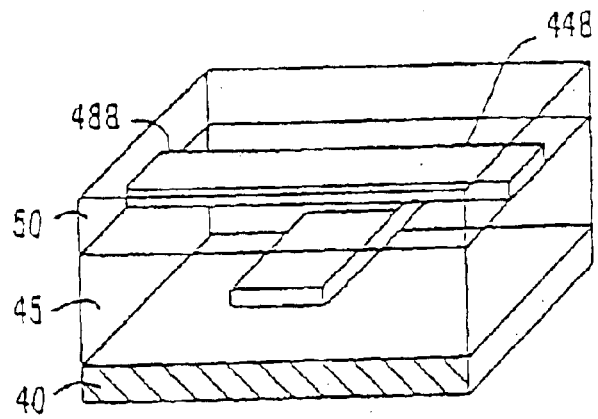
FIG. 25 is an illustration showing a third elastomer layer applied on top of the second elastomeric layer and over the second line of sacrificial layer of FIG. 24, thereby encapsulating the second line of sacrificial layer between the elastomeric structure of FIG. 22 and the third elastomeric layer.

Referring to FIG. 23, a second sacrificial layer 48A is then deposited over elastomeric structure 45. Referring to FIG. 24, a portion of second sacrificial layer 48A is removed, leaving only a second sacrificial layer 48B on top of elastomeric structure 45 as shown. Referring to FIG. 25, a third elastomeric layer 50 is then deposited over the top of elastomeric structure 45 (comprised of second elastomeric layer 42 and first line of sacrificial layer 44B) and second sacrificial layer 48B as shown, thereby encasing the second line of sacrificial layer 48B between elastomeric structure 45 and third elastomeric layer 50.

Figure 26:
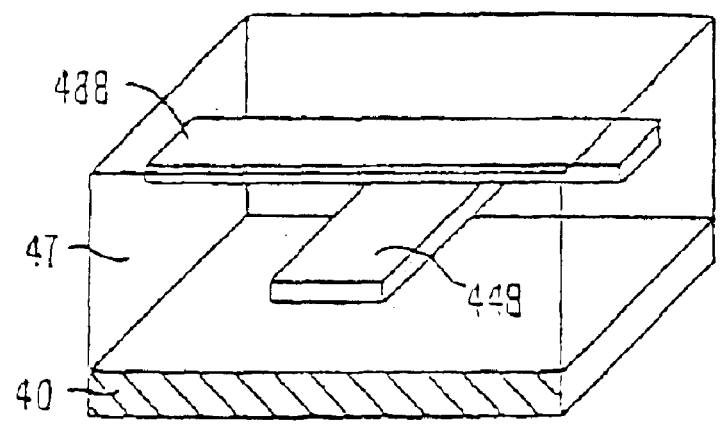
FIG. 26 corresponds to FIG. 25, but shows the third elastomeric layer cured so as to be bonded to the monolithic structure composed of the previously bonded first and second elastomer layers.
Figure 27:
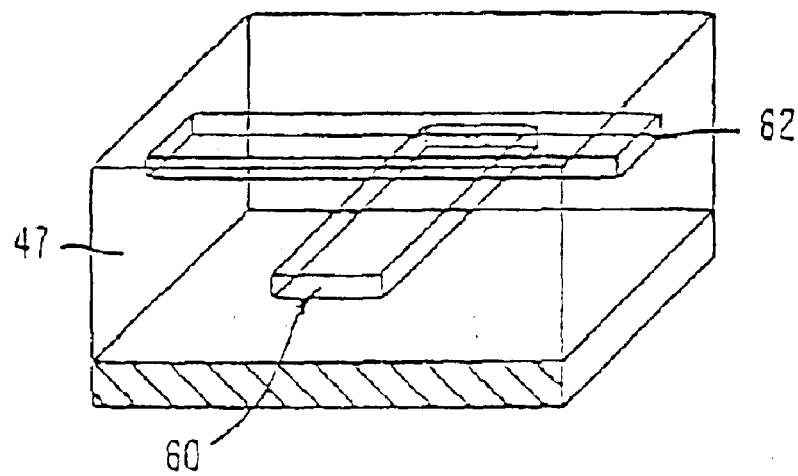
FIG. 27 corresponds to FIG. 26, but shows the first and second lines of sacrificial layer removed so as to provide two perpendicular overlapping, but not intersecting, flow channels passing through the integrated elastomeric structure.
Figure 28:
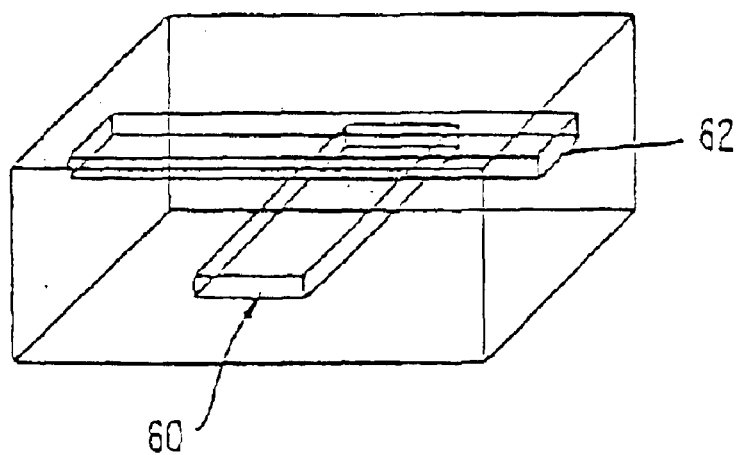
FIG. 28 is an illustration showing the system of FIG. 27, but with the planar substrate thereunder removed.

Referring to FIG. 26, third elastomeric layer 50 and elastomeric structure 45 (comprising first elastomeric layer 42 and second elastomeric layer 46 bonded together) is then bonded together forming a monolithic elastomeric structure 47 having sacrificial layers 44B and 48B passing therethrough as shown. Referring to FIG. 27, sacrificial layers 44B and 48B are then removed (for example, by dissolving in a solvent) such that a flow channel 60 and a control channel 62 are provided in their place, passing through elastomeric structure 47 as shown. And referring to FIG. 28, planar substrate 40 can be removed from the bottom of the integrated monolithic structure.

Microfabricated Polymers

Microfabricated refers to the size of features of a polymer fabricated in accordance with an embodiment of the present invention. In general, variation in at least one dimension of microfabricated structures is controlled to the micron level, with at least one dimension being microscopic (i.e. below 1000 $\mu$m). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, channels (flow channels and controls channels) 30, 32, 60 and 62 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels 30, 32, 60 and 62 have widths of about 1 to 1000 microns. A non-exclusive list of other ranges of widths of channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 $\mu$m, 1 $\mu$m, 2 $\mu$m, 5 $\mu$m, 10 $\mu$m, 20 $\mu$m, 30 $\mu$m, 40 $\mu$m, 50 $\mu$m, 60 $\mu$m, 70 $\mu$m, 80 $\mu$m, 90 $\mu$m, 100 $\mu$m, 110 $\mu$m, 120 $\mu$m, 130 $\mu$m, 140 $\mu$m, 150 $\mu$m, 160 $\mu$m, 170 $\mu$m, 180 $\mu$m, 190 $\mu$m, 200 $\mu$m, 210 $\mu$m, 220 $\mu$m, 230 $\mu$m, 240 $\mu$m, and 250 $\mu$m.

Channels 30, 32, 60, and 62 have depths of about 1 to 100 microns. A non-exclusive list of other ranges of depths of channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 $\mu$m, 0.02 $\mu$m, 0.05 $\mu$m, 0.1 $\mu$m, 0.2 $\mu$m, 0.5 $\mu$m, 1 $\mu$m, 2 $\mu$m, 3 $\mu$m, 4 $\mu$m, 5 $\mu$m, 7.5 $\mu$m, 10 $\mu$m, 12.5 $\mu$m, 15 $\mu$m, 17.5 $\mu$m, 20 $\mu$m, 22.5 $\mu$m, 25 $\mu$m, 30 $\mu$m, 40 $\mu$m, 50 $\mu$m, 75 $\mu$m, 100 $\mu$m, 150 $\mu$m, 200 $\mu$m, and 250 $\mu$m.

The channels are not limited to these specific dimension ranges and examples given above, and can vary in width in order to affect the magnitude of force required to deflect the elastomeric segment. Elastomeric structures which include portions having channels of even greater width than described above are also contemplated by the present invention, and examples of applications of utilizing such wider flow channels include fluid reservoir and mixing channel structures.

Elastomeric layer 22 can be cast thick for mechanical stability. In an exemplary embodiment, layer 22 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, elastomeric segment 25 of FIG. 17B separating flow channel 30 and control channel 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary elastomeric segment thicknesses include 0.01 $\mu$m, 0.02 $\mu$m, 0.03 $\mu$m, 0.05 $\mu$m, 0.1 $\mu$m, 0.2 $\mu$m, 0.3 $\mu$m, 0.5 $\mu$m, 1 $\mu$m, 2 $\mu$m, 3 $\mu$m, 5 µm, 7.5 µm, 10 µm, 12.5 µm, 15 µm, 17.5 µm, 20 µm, 22.5 µm, 25 µm, 30 µm, 40 µm, 50 µm, 75 µm, 100 µm, 150 µm, 200 µm, 250 µm, 300 µm, 400 µm, 500 µm, 750 µm, and 1000 µm Similarly, first elastomeric layer 42 can have a preferred thickness about equal to that of elastomeric layer 20 or 22; second elastomeric layer 46 can have a preferred thickness about equal to that of elastomeric layer 20; and third elastomeric layer 50 can have a preferred thickness about equal to that of elastomeric layer 22.

One particular aspect of the present invention provides microfluidic devices comprising a microfabricated flow channel which is located within the polymer matrix and defines an inner surface. Optionally, the microfluidic devices comprise a plurality of microfabricated flow channels. The microfluidic devices can also have a plurality of reservoirs for storing various reagents such as solutions, solvents, and/or samples. In addition, the microfluidic devices can have pumps and valves for controlling flow of the reagents. The flow channel can also have a window to allow optical interrogation.

Use of microfluidic devices of the present invention reduces the sample size and the amount of eluent needed as well as providing a sufficiently small flow rate for microscale chromatography processes, e.g., OTLC or PCLC.

Polymers of the present invention are preferably produced from polymerization of at least two different components. These polymers are preferably produced using an off ratio of each component. Exemplary off ratio polymers which are useful in the present invention include, but are not limited to:

silicone polymers which can be produced from monomers comprising a silane and an olefin reactive polymerizable functional groups, e.g., GE's RV615, and Dow Corning's Sylgard 184, 182 186;

polyurethane polymers which can be produced from monomers comprising a diisocyanate and an di-alcohol or di-amine reactive polymerizable functional groups, e.g., Synair's 2612020,261S111 and 261S333 or Uniroyal's Vibrathane 504;

polyisoprene, polybutadiene, polychloroprene which are polymerized from diene monomers, and therefore have one double bond per monomer when polymerized. This double bond on the surface allows the covalent bonding of the stationary phase compound to the polymer. The polymer rubber can then be vulcanized to form a soft elastomer product.

styrene butadiene rubber which is produced from an olefin and a diene reactive functional groups of styrene and butadiene, respectively; The double bond presented in the pre-crosslinked polymer allows the surface of the polymer to be modified.

Preferable, polymers of the present invention comprise off ratio polymer derived from at least two PDMS resins containing silane and olefin functional groups, respectively.

The amount of each component is selected such that the relative molar ratio of the reactive functional group of one monomeric unit is present in excess of the other(s). In this manner, a significant amount of the reactive functional group of the excess monomer remains unreacted within the polymer. Preferably, at least about 1% of the reactive functional group of the excess monomer remains unreacted within the polymer, more preferably at least about 6%, and most preferably at least about 30%. Alternatively, polymers of the present invention comprise one unreacted reactive functional group per about 10,000 monomeric units, preferably per about 1,000 monomeric units, and more preferably per about 100 monomeric units.

In one particular embodiment, the polymer is derived from two monomer/prepolymer components. Preferably, the polymer is produced by combining the respective monomer/prepolymer at a relative molar ratio of from 1:10 to about 1:3, more preferably at a relative molar ratio of from 1:5 to about 1:2, and most preferably at a relative molar ratio of from 1:2 to about 1:1.1.

Other Suitable Polymer Materials

Allcock et al., Contemporary Polymer Chemistry, $2^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. Elastomeric materials having a Young's modulus of between about 1 Pa to about 1 TPa, more preferably between about 10 Pa to about 100 GPa, more preferably between about 20 Pa to about 1 GPa, more preferably between about 50 Pa to about 10 MPa, and more preferably between about 100 Pa to about 1 MPa are useful in accordance with the present invention, although elastomeric materials having a Young's modulus outside of these ranges could also be utilized depending upon the needs of a particular application.

The systems of the present invention can be fabricated from a wide variety of elastomers, preferably off ratio polymers. For example, elastomeric layers 20, 22, 42, 46 and 50 can preferably be fabricated from silicone rubber. In some applications, microstructures of the present systems are fabricated from an elastomeric polymer such as GE RTV 615 (formulation), a vinyl-silane crosslinked (type) silicone elastomer (family). An important requirement for the preferred method of fabrication is the ability to produce a polymer with unreacted reactive functional group. More preferably, the fabrication process produces layers of elastomers which can be bonded together. In the case of multilayer soft lithography, layers of elastomer are cured separately and then bonded together. This scheme requires that cured layers possess sufficient reactivity to bond together. Either the layers can be of the same type, and are capable of bonding to themselves, or they can be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microstructures. Variations in the materials used most likely are driven by the need for particular material properties, e.g., stiffness, gas permeability, or temperature stability.

Common elastomeric polymers include, but are not limited to, polyisoprene, polybutadiene, polychloroprene, polyisobutylene, poly(styrene-butadiene-styrene), the polyurethanes, and silicones. The following is a non-exclusive list of elastomeric materials which can be utilized in connection with the present invention: polyisoprene, polybutadiene, polychloroprene, polyisobutylene, poly (styrene-butadiene-styrene), the polyurethanes, and silicone polymers; or poly(bis(fluoroalkoxy)phosphazene) (PNF, Eypel-F), poly(carborane-siloxanes) (Dexsil), poly (acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

In addition, polymers incorporating materials such as chlorosilanes or methyl-, ethyl-, and phenylsilanes, and polydimethylsiloxane (PDMS) such as Dow Chemical Corp. Sylgard 182, 184 or 186, or aliphatic urethane diacrylates such as (but not limited to) Ebecryl 270 or Irr 245 from UCB Chemical can also be used.

In some methods, elastomers can also be "doped" with uncross-linkable polymer chains of the same class. For instance RTV 615 can be diluted with GE SF96-50 Silicone Fluid. This serves to reduce the viscosity of the uncured elastomer and reduces the Young's modulus of the cured elastomer. Essentially, the crosslink-capable polymer chains are spread further apart by the addition of "inert" polymer chains, so this is called "dilution". RTV 615 cures at up to 90% dilution, with a dramatic reduction in Young's modulus.

Other examples of doping of elastomer material can include the introduction of electrically conducting or magnetic species. Should it be desired, doping with fine particles of material having an index of refraction different than the elastomeric material (i.e. silica, diamond, sapphire) is also contemplated as a system for altering the refractive index of the material. Strongly absorbing or opaque particles can be added to render the elastomer colored or opaque to incident radiation. This can conceivably be beneficial in an optically addressable system.

Multilayer Construction

Soft lithographic bonding can be used to construct an integrated system which contains multiple channels (e.g., flow channels and/or control channels). A heterogenous bonding can be used in which different layers are of different chemistries. For example, the bonding process used to bind respective elastomeric layers together can comprise bonding together two layers of RTV 615 silicone. RTV 615 silicone is a two-part addition-cure silicone rubber. Part A contains vinyl groups and catalyst; part B contains silane (Si-H) groups. The conventional ratio for RTV 615 is 10A:1B. For bonding, one layer can be made with 30A:1B (i.e. excess vinyl groups) and the other with 3A:1B (i.e. excess silane groups). Each layer is cured separately. When the two layers are brought into contact and heated at elevated temperature, they bond irreversibly forming a monolithic elastomeric substrate.

A homogenous bonding can also be used in which all layers are of the same chemistry. For example, elastomeric structures are formed utilizing Sylgard 182, 184 or 186, or aliphatic urethane diacrylates such as (but not limited to) Ebecryl 270 or Irr 245 from UCB Chemical. For example, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhesion to glass.

In some applications, two-layer elastomeric structures were fabricated from a combination of 25% Ebe 270/50% Irr245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhered to glass.

Where encapsulation of sacrificial layers is employed to fabricate the elastomer structure as described above in FIGS. 18–28, bonding of successive elastomeric layers can be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer creates a monolithic elastomeric structure in which a bond is formed between the elastomeric layers.

Referring to the first method of FIGS. 11 to 17B, first elastomeric layer 20 can be created by spin-coating an RTV mixture on microfabricated mold 12 at 2000 rpm for 30 seconds yielding a thickness of approximately 40 microns. Second elastomeric layer 22 can be created by spin-coating an RTV mixture on microfabricated mold 11. Both layers 20 and 22 can be separately baked or cured at about 80° C. for 1.5 hours. The second elastomeric layer 22 can be bonded onto first elastomeric layer 20 at about 80° C. for about 1.5 hours.

Micromachined molds 10 and 12 can be patterned sacrificial layer on silicon wafers. For example, a Shipley SJR 5740 sacrificial layer can be spun at 2000 rpm, patterned with a high resolution transparency film as a mask and then developed yielding an inverse channel of approximately 10 microns in height. When baked at approximately 200° C. for about 30 minutes, the sacrificial layer reflows and the inverse channels become rounded. Optionally, the molds can be treated with trimethylchlorosilane (TMCS) vapor for about a minute before each use in order to prevent adhesion of silicone rubber.

Operation of the Microfabricated Components

Figure 29A:
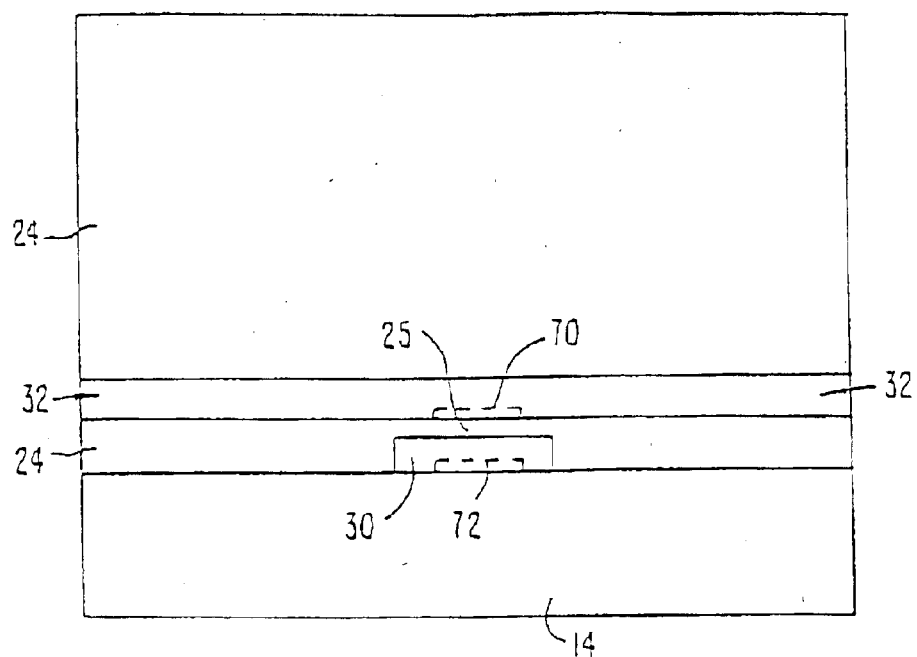
FIG. 29A is a front sectional view corresponding to FIG. 17A, showing an open flow channel.
Figure 29B:
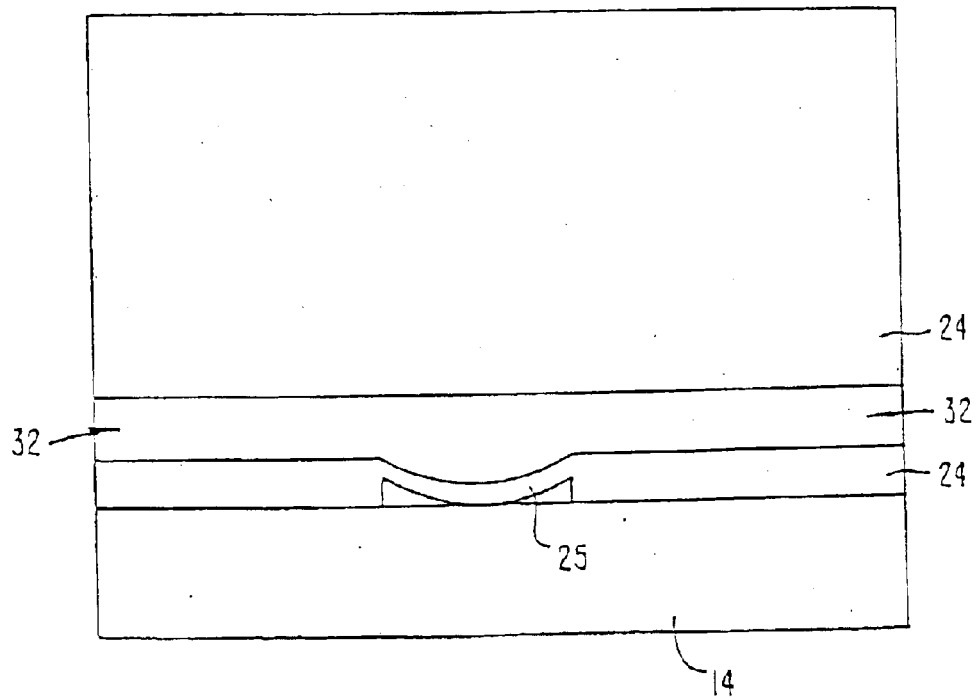
FIG. 29B corresponds to FIG. 17A, but shows a first flow channel closed by pressurization in second flow channel.

FIGS. 29A and 29B together show the closing of a flow channel by pressurizing a control channel, with FIG. 29A (a front sectional view cutting through flow channel 32 in corresponding FIG. 17A), showing an open flow channel 30; with FIG. 29B showing flow channel 30 closed by pressurization of the control channel 32.

Referring to FIG. 29A, flow channel 30 and control channel 32 are shown. Elastomeric segment 25 separates the channels, forming the top of flow channel 30 and the bottom of control channel 32. As can be seen, flow channel 30 is "open".

As can be seen in FIG. 29B, pressurization of control channel 32 (either by gas or liquid introduced therein) causes elastomeric segment 25 to deflect downward, thereby pinching off flow channel 30. Accordingly, by varying the pressure in control channel 32, an actuable valve system is provided such that flow channel 30 can be opened or closed by moving elastomeric segment 25 as desired. (For illustration purposes only, channel 30 in FIG. 29B is shown in a "mostly closed" position, rather than a "fully closed" position).

It is to be understood that exactly the same valve opening and closing methods can be achieved with channels 60 and 62. Since such valves are actuated by moving the roof of the channels themselves (i.e., moving elastomeric segment 25), valves and pumps produced by this technique have a truly zero dead volume, and switching valves made by this technique have a dead volume approximately equal to the active volume of the valve, for example, about 100×100×10 $\mu$m=100 pL. Such dead volumes and areas consumed by the moving elastomeric segment are approximately two orders of magnitude smaller than known conventional microvalves. Smaller and larger valves and switching valves are contemplated in the present invention, and a non-exclusive list of ranges of dead volume includes 1 aL to 1 $\mu$L, 100 aL to 100 nL, 1 fL to 10 nL, 100 fL to 1 nL, and 1 pL to 100 pL The extremely small volumes capable of being delivered by pumps and valves in accordance with the present invention represent a substantial advantage. Specifically, the smallest known volumes of fluid capable of being manually metered is around 0.1 $\mu$l. The smallest known volumes capable of being metered by automated systems is about ten-times larger (1 $\mu$l). Utilizing pumps and valves of the present invention, volumes of liquid of 10 nl or smaller can routinely be metered and dispensed. The accurate metering of extremely small volumes of fluid enabled by the present invention allows chromatography separation of an extremely small amount of the sample.

Figure 30:
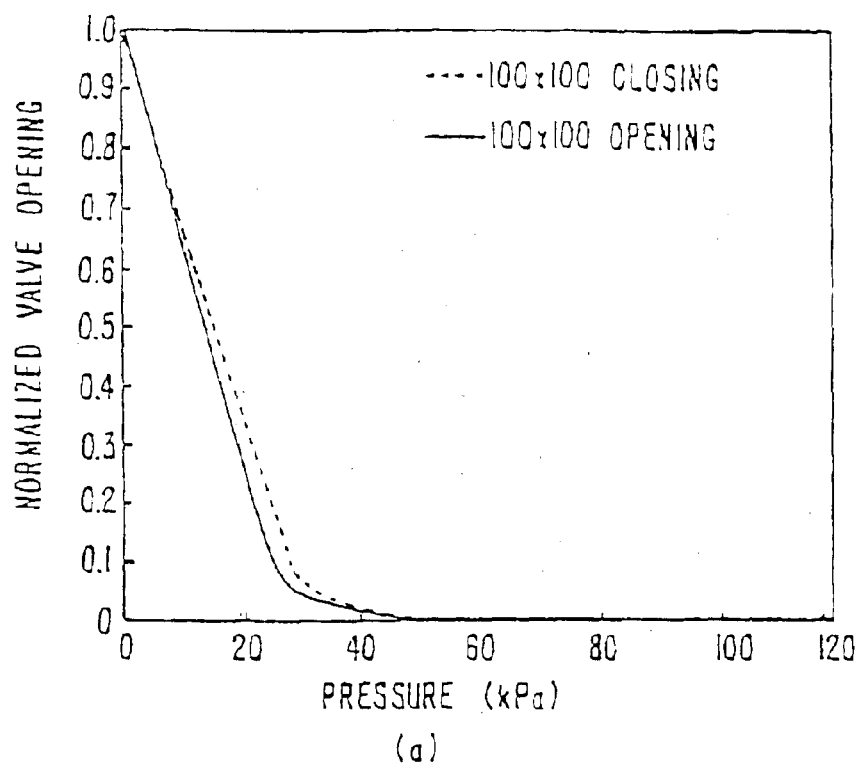
FIGS. 30a and 30b illustrate valve opening vs. applied pressure for various flow channel dimensions.
Figure 30:
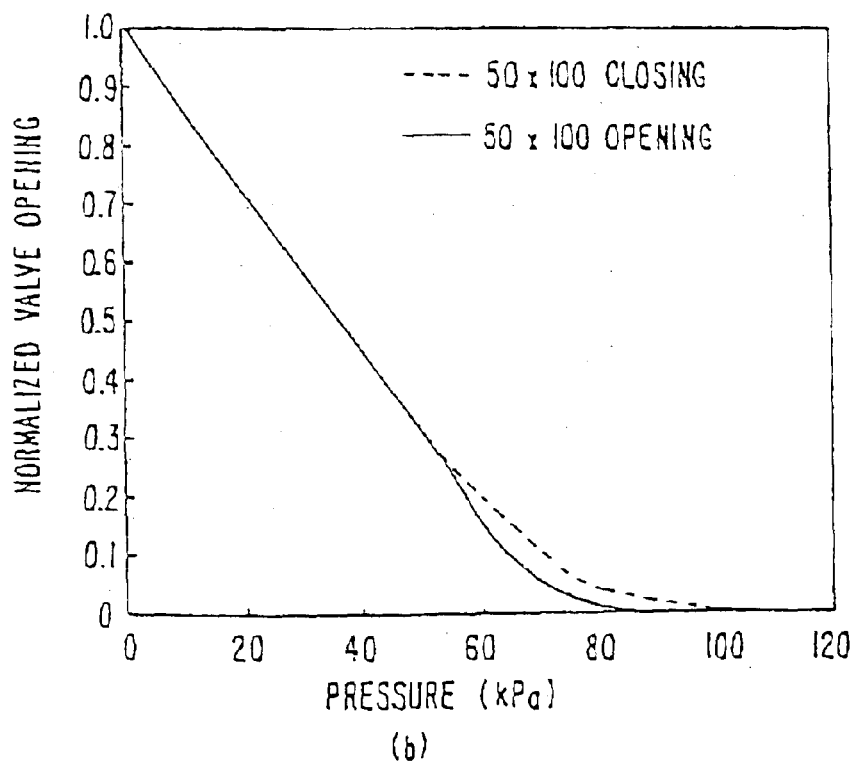

FIGS. 30a and 30b illustrate valve opening vs. applied pressure for a 100 $\mu$m wide flow channel 30 and a 50 $\mu$m wide control channel 32, respectively. The elastomeric segment of this device was formed by a layer of General Electric Silicones RTV 615 having a thickness of approximately 30 $\mu$m and a Young's modulus of approximately 750 kPa. FIGS. 30a and 30b show the extent of opening of the valve to be substantially linear over most of the range of applied pressures.

Air pressure was applied to actuate the elastomeric segment of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

The response of valves of the present invention is substantially linear over a large portion of its range of travel, with minimal hysteresis. While valves and pumps do not require linear actuation to open and close, linear response does allow valves to more easily be used as metering devices. In some applications, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation can be easily determined from the pressure in the flow channel. If actuation is linear, increased pressure in the flow channel can be countered by adding the same pressure (force per unit area) to the actuated portion of the valve.

Control and Pump Systems

Figure 31A:
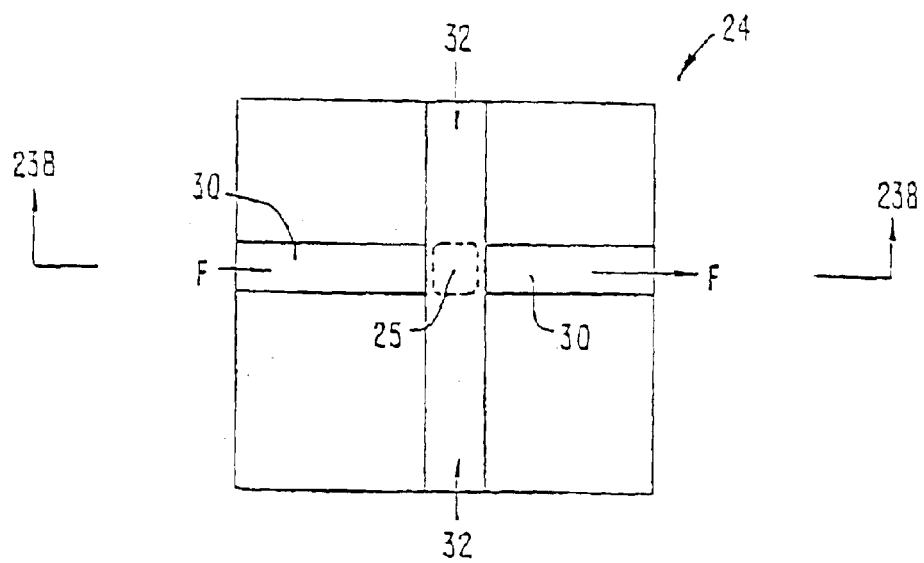
FIG. 31A is a top schematic view of an on/off valve.
Figure 32A:
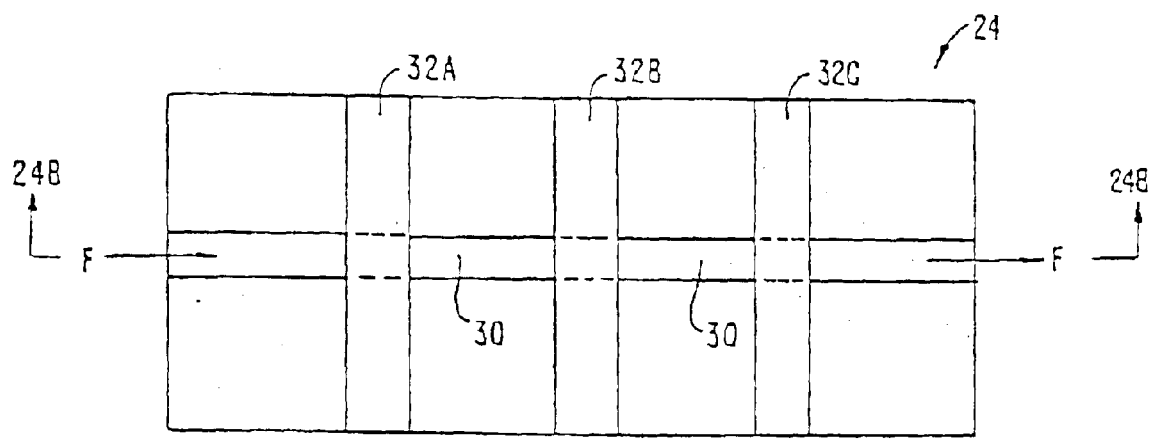
FIG. 32A is a top schematic view of a peristaltic pumping system.
Figure 31B:
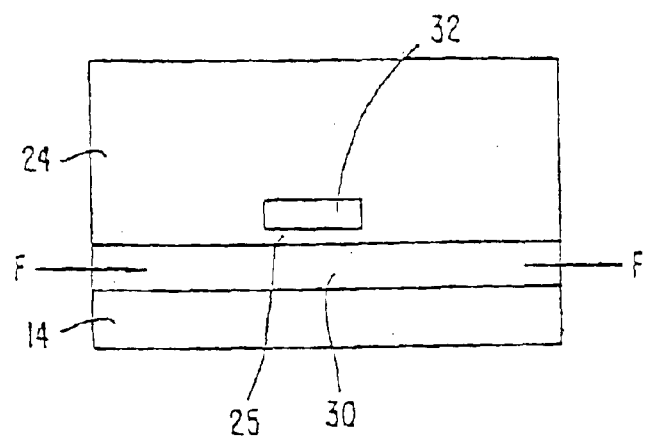
FIG. 31B is a sectional elevation view along line 23B—23B in FIG. 31A
Figure 32B:
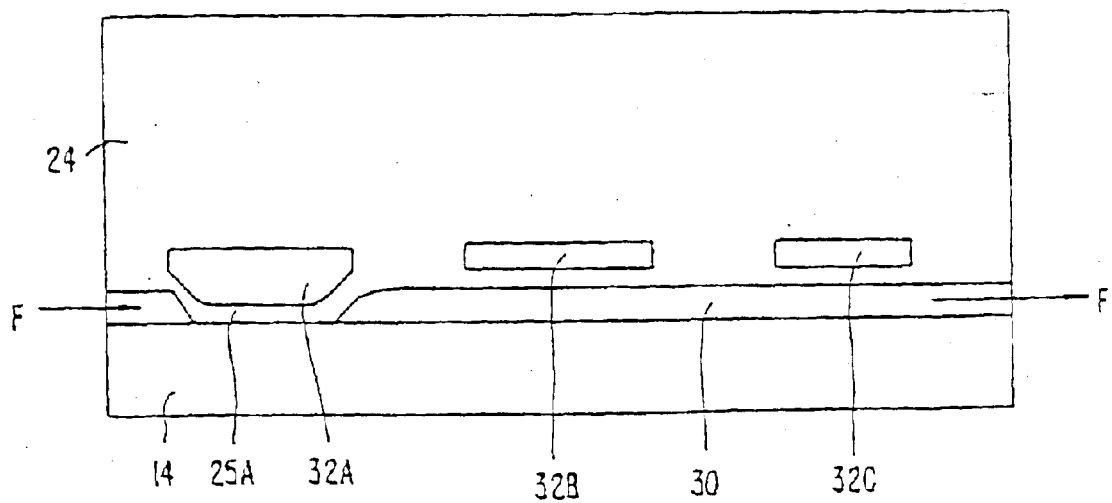
FIG. 32B is a sectional elevation view along line 24B—24B in FIG. 32A
Figure 33:
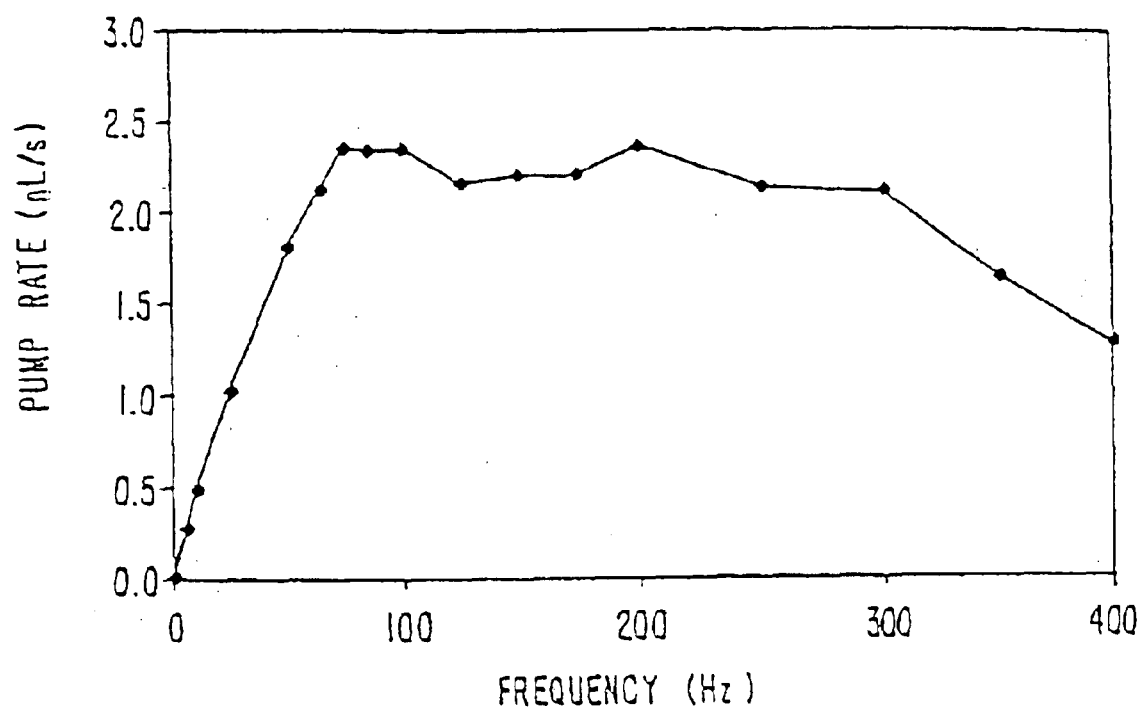
FIG. 33 is a graph showing experimentally achieved pumping rates vs. frequency for an embodiment of the peristaltic pumping system of FIGS. 32A and 32B.

FIGS. 31A and 31B show a views of a single on/off valve (e.g., control system), identical to the systems set forth above, (for example in FIG. 17A). FIGS. 32A and 32B shows a peristaltic pumping system (e.g., a material delivery system) comprised of a plurality of the single addressable on/off valves as seen in FIGS. 31A and 31B, but networked together. FIG. 33 is a graph showing experimentally achieved pumping rates vs. frequency for the peristaltic pumping system of FIGS. 32A and 32B.

Referring first to FIGS. 31A and 31B, a schematic of channels 30 and 32 is shown. Flow channel 30 preferably has a fluid (or gas) flow F passing therethrough. Control channel 32, which crosses over flow channel 30, is pressurized such that elastomeric segment separating the channels is depressed into the path of flow channel 30, shutting off the passage of flow F therethrough, as described above.

Referring to FIGS. 32A and 32B, a system for peristaltic pumping is provided, as follows. A flow channel 30 has a plurality of generally parallel control channels 32A, 32B and 32C passing thereover. By pressurizing control line 32A, flow F through flow channel 30 is shut off under elastomeric segment 25A at the intersection of control line 32A and flow channel 30. Similarly, (but not shown), by pressurizing control line 32B, flow F through flow channel 30 is shut off under elastomeric segment 25B at the intersection of control line 32B and flow channel 30, etc. Each of control lines 32A, 32B, and 32C is separately addressable. Therefore, peristalsis can be actuated by the pattern of actuating 32A and 32C together, followed by 32A, followed by 32A and 32B together, followed by 32B, followed by 32B and C together, etc. This corresponds to a successive "101, 100, 110, 010, 011, 001" pattern, where "0" indicates "valve open" and "1" indicates "valve closed." This peristaltic pattern is also known as a 120° pattern (referring to the phase angle of actuation between three valves). Other peristaltic patterns are equally possible, including 60° and 90° patterns.

Using this process, a pumping rate of 2.35 nL/s was measured by measuring the distance traveled by a column of water in thin (0.5 mm i.d.) tubing; with 100×100×10 $\mu$m valves under an actuation pressure of 40 kPa. As shown in FIG. 24, the pumping rate increased with actuation frequency until approximately at about 75 Hz, and from about 75 Hz to above 200 Hz the pumping rate was nearly constant. The valves and pumps are also quite durable and the elastomeric segment, control channels, or bond have not been observed to fail. Moreover, none of the valves in the peristaltic pump described herein show any sign of wear or fatigue after more than 4 million actuations.

Non-Elastomer Based Polymers

As discussed above, while elastomers are preferred materials for fabricating the microfluidic devices of the present invention, non-elastomer based microfluidic devices can also be used in the apparatuses of the present invention. In some applications, the chromatography apparatuses utilize microfluidics based on conventional micro-electro mechanical system (MEMS) technology. Methods of producing conventional MEMS microfluidic systems such as bulk micro-machining and surface micro-machining have been described, e.g., in Terry et al., A Gas Chromatography Air Analyzer Fabricated on a Silicon Wafer, IEEE Trans. on Electron Devices, v. ED-26, pp. 1880–1886, 1979; and Berg et al., Micro Total Analysis Systems, New York, Kluwer, 1994, all of which are incorporated herein by reference in their entirety.

Bulk micro-machining is a subtractive fabrication method whereby single crystal silicon is lithographically patterned and then etched to form three-dimensional structures. For example, bulk micromachining technology, which includes the use of glass wafer processing, silicon-to-glass wafer bonding, has been commonly used to fabricate individual microfluidic components. This glass-bonding technology has also been used to fabricate microfluidic systems.

Surface micro-machining is an additive method where layers of semiconductor-type materials such as polysilicon, silicon nitride, silicon dioxide, and various metals are sequentially added and patterned to make three-dimensional structures. Surface micromachining technology can be used to fabricate individual fluidic components as well as microfluidic systems with on-chip electronics. In addition, unlike bonded-type devices, hermetic channels can be built in a relatively simple manner using channel walls made of polysilicon (see, e.g., Webster et al., Monolithic Capillary Gel Electrophoresis Stage with On-Chip Detector, in International Conference on Micro Electromechanical Systems, MEMS 96, pp. 491–496, 1996), silicon nitride (see, e.g., Mastrangelo et al., Vacuum-Sealed Silicon Micromachined Incandescent Light Source, in Intl. Electron Devices Meeting, IDEM 89, pp. 503–506, 1989), and silicon dioxide.

In some applications, electrokinetic flow based microfluidics can be employed in the chromatography apparatuses of the present invention. Briefly, these systems direct reagents flow within an interconnected channel and/or chamber containing structure through the application of electrical fields to the reagents. The electrokinetic systems concomitantly regulate voltage gradients applied across at least two intersecting channels. Such systems are described, e.g., in WO 96/04547 and U.S. Pat. No. 6,107,044.

Electrokinetic flow based microfluidic devices can have a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., "T" intersection.

In some electrokinetic flow based apparatuses, at least three intersecting channels having at least four unintersected termini are present. In a basic cross channel structure, where a single horizontal channel is intersected and crossed by a single vertical channel, controlled electrolinetic transport operates to direct reagent flow through the intersection, by providing constraining flows from the other channels at the intersection. Simple electrokinetic flow of this reagent across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A microfluidic chromatography apparatus for separating an analyte in a sample fluid comprising:
   (a) a microfabricated fluid delivery system which is produced from a material comprising an elastomeric polymer, wherein said fluid deliver system comprises:
      (i) a microfluidic flow channel comprising a flow channel inlet for introducing the fluid into said flow channel and a flow channel outlet,
      (ii) a flow control channel,
      (iii) a flow control valve comprised of a flow control elastomeric segment that is disposed in between said flow channel and said flow control channel to regulate fluid flow through said flow channel, wherein said flow control valve is deflectable into or retractable from said flow channel upon which said flow control valve operates in response to an actuation force applied to said flow control channel, said flow control elastomeric segment when positioned in said flow channel restricting fluid flow therethrough, and
      (iv) a flow control channel actuation system operatively interconnected to said flow control channel for applying an actuation force to said flow control channel; and
   (b) a chromatography column comprising:
      (i) a stationary phase which is capable of separating at least a portion of the analyte from the sample fluid,
      (ii) a column inlet which is in fluid communication with said flow channel outlet, and
      (iii) a column outlet through which a separated fluid exits the chromatography column.

2. The microfluidic chromatography apparatus of claim 1, wherein said elastomeric polymer is selected from the group consisting of poly(carborane-siloxanes), poly(bis (fluoroalkoxy)phosphazene), poly(acrylonitrile-butadiene), poly(1-butene), poly(chlorotrifluoroethylene-vinylidene fluoride) copolymers, poly(ethyl vinyl ether), poly (vinylidene fluoride), poly(vinylidene fluoride-hexafluoropropylene) copolymer, elastomeric polyvinylchloride, polysulfone, polycarbonate, polymethylmethacrylate, polytertrafluoroethylene, polydimethylsiloxane, polydimethylsiloxane copolymer, and aliphatic urethane diacrylate.

3. The microfluidic chromatography apparatus of claim 1, wherein said fluid delivery system further comprises a peristaltic pump which is comprised of one or more of said flow control valves.

4. The microfluidic chromatography apparatus of claim 3, wherein said fluid delivery system further comprises an eluent inlet which is in fluid communication with said flow channel inlet for introducing an eluent to said flow channel.

5. The microfluidic chromatography apparatus of claim 1, wherein said chromatography column is a microfluidic chromatography device comprising a chromatography channel having an inner surface.

6. The microfluidic chromatography apparatus of claim 5, wherein said stationary phase is covalently attached to said inner surface.

7. The microfluidic chromatography apparatus of claim 5, wherein said chromatography column comprises a microfabricated rotary channel comprising:

a rotary channel inlet;

(a) a rotary channel outlet;

(b) a rotary control channel;

(c) a rotary inlet control valve comprised of an elastomeric segment of said rotary inlet control channel that is disposed in between said rotary channel inlet and said rotary control channel to regulate fluid flow into said rotary channel, wherein said rotary inlet control valve is deflectable into or retractable from said rotary channel inlet upon which said rotary inlet control valve operates in response to an actuation force applied to said rotary control channel, said elastomeric segment of said rotary inlet control channel when positioned in said rotary channel inlet restricting fluid flow therethrough;

(d) a rotary outlet control valve comprised of an elastomeric segment of said rotary outlet control channel that is disposed in between said rotary channel outlet and said rotary control channel to regulate fluid flow out of said rotary channel, wherein said rotary outlet control valve is deflectable into or retractable from said rotary channel outlet upon which said rotary outlet control valve operates in response to an actuation force applied to said rotary control channel, said elastomeric segment of said rotary control channel outlet when positioned in said rotary channel outlet restricting fluid flow therethrough;

(e) a rotary pump valve comprised of an elastomeric segment of said rotary pump that is disposed in between said rotary channel and said rotary pump control channel to regulate fluid flow through said rotary channel, wherein said rotary pump valve is deflectable into or retractable from said rotary channel upon which said rotary pump valve operates in response to an actuation force applied to said rotary pump control channel, said elastomeric segment of said rotary pump when positioned in said rotary channel restricting fluid flow therethrough; and (f) a rotary control channel actuation system operatively interconnected to said rotary control channel for applying an actuation force to said rotary control channel.

8. The microfluidic chromatography apparatus of claim 4, wherein said flow channel inlet further comprises:

a sample reservoir comprising a sample reservoir inlet channel which is in fluid communication with said flow channel;

a sample reservoir inlet control channel;

a sample reservoir inlet control valve for opening and closing fluid communication between said sample reservoir and said flow channel, wherein said sample reservoir inlet control valve comprises an elastomeric segment of said sample reservoir inlet control channel that is disposed in between said sample reservoir control channel and said sample reservoir inlet channel to regulate fluid flow through said sample reservoir inlet channel, wherein said sample reservoir inlet control valve is deflectable into or retractable from said sample reservoir inlet channel upon which said sample reservoir inlet control valve operates in response to an actuation force applied to said sample reservoir inlet control channel, said elastomeric segment of said sample reservoir inlet control channel when positioned in said sample reservoir inlet channel restricting fluid flow therethrough; and an sample reservoir inlet control channel actuation system operatively interconnected to said sample reservoir inlet control channel for applying an actuation force to said sample reservoir inlet control channel.

9. The microfluidic chromatography apparatus of claim 4, wherein said eluent inlet further comprises:

an eluent reservoir comprising an eluent reservoir inlet channel;

an eluent reservoir inlet control channel;

an eluent reservoir inlet control valve for opening and closing fluid communication between said eluent reservoir and said flow channel, wherein said eluent reservoir inlet control valve comprises an elastomeric segment of said eluent reservoir inlet control channel that is disposed in between said eluent reservoir inlet control channel and said eluent reservoir inlet channel to regulate fluid flow through said eluent reservoir inlet channel, wherein said eluent reservoir inlet control valve is deflectable into or retractable from said eluent reservoir inlet channel upon which said eluent reservoir inlet control valve operates in response to an actuation force applied to said eluent reservoir inlet control channel, said elastomeric segment of said eluent reservoir inlet control valve when positioned in said eluent reservoir inlet channel restricting fluid flow therethrough;

an eluent reservoir inlet control channel actuation system operatively interconnected to said eluent reservoir inlet control channel for applying an actuation force to said eluent reservoir inlet control channel.

10. The microfluidic chromatography apparatus of claim 1, wherein said column outlet is in fluid communication with a sample detection system inlet.

11. The microfluidic chromatography apparatus of claim 1, wherein said chromatography column is an open tubular liquid chromatography column or a packed capillary liquid chromatography column.

12. The microfluidic chromatography apparatus of claim 1, wherein said flow channel is located on an interface between a solid substrate and the elastomeric polymer such that an inner surface of said flow channel comprises an elastomeric polymer portion and a solid substrate portion.

13. The microfluidic chromatography apparatus of claim 12, wherein the stationary phase is attached to the solid substrate portion of the flow channel inner surface.

14. The microfluidic chromatography apparatus of claim 13, wherein the elastomeric polymer portion of the flow channel inner surface comprises a surface coating that reduces a non-specific binding of the analyte.

* * * * *